(12) United States Patent
Ishida et al.

(10) Patent No.: US 7,696,333 B1
(45) Date of Patent: Apr. 13, 2010

(54) PROMOTER IN THE PRESENCE OF ORGANIC ACID AND UTILIZATION THEREOF

(75) Inventors: Nobuhiro Ishida, Aichi-gun (JP); Kenro Tokuhiro, Aichi-gun (JP); Eiji Nagamori, Nisshin (JP); Haruo Takahashi, Ohgaki (JP); Satoshi Saitoh, Nishikamo-gun (JP); Tohru Ohnishi, Toyota (JP)

(73) Assignees: Kabuhsiki Kaisha Toyota Chuo Jenjyusho, Aichi-gun (JP); Toyota Jidosha Kabuhsiki Kaisha, Toyota-shi (JP)

( * ) Notice: Subject to any disclaimer, the term of this patent is extended or adjusted under 35 U.S.C. 154(b) by 679 days.

(21) Appl. No.: 10/578,614

(22) PCT Filed: Nov. 5, 2004

(86) PCT No.: PCT/JP2004/016799

§ 371 (c)(1),
(2), (4) Date: May 8, 2006

(87) PCT Pub. No.: WO2005/045024

PCT Pub. Date: May 19, 2005

(30) Foreign Application Priority Data

Nov. 7, 2003 (JP) .............................. 2003-379076

(51) Int. Cl.
*C12N 15/11* (2006.01)
*C12N 15/63* (2006.01)
*C12N 1/19* (2006.01)
*C12P 9/00* (2006.01)
*C12N 9/00* (2006.01)

(52) U.S. Cl. ................. 536/23.1; 435/320.1; 435/254.2; 435/131

(58) Field of Classification Search ........................ None
See application file for complete search history.

(56) References Cited

U.S. PATENT DOCUMENTS

2003/0228671 A1* 12/2003 Hause et al. ................. 435/161

FOREIGN PATENT DOCUMENTS

| JP | 2003-164295 | 6/2003 |
|---|---|---|
| WO | 84/04538 | 11/1984 |
| WO | WO 99/14335 | * 3/1999 |
| WO | 2001/38549 | 5/2001 |
| WO | 02/00880 | 1/2002 |
| WO | 02/064766 | 8/2002 |

OTHER PUBLICATIONS

Hauf, Joerg et al., "Simultaneous genomic overexpression of seven glycolytic enzymes in the yeast *Saccharomyces cerevisiae*", Enzyme and Microbial Technology, vol. 26, No. 9-10, pp. 688-698, 2000.
Riou, C. et al., "Stationary-Phase Gene Expression in *Saccharomyces cerevisiae* During Wine Fermentation", Yeast, vol. 13, No. 10, pp. 903-915, 1997.
Wu, Ke et al., "Expression and subcellular localization of a membrane protein related to Hsp30p in *Saccharomyces cerevisiae*", Biochimica Acta, vol. 1463, No. 2, pp. 477-482, 2000.
Adachi, Eri, et al., "Modification of Metabolic Pathways of *Saccharomyces cerevisiae* by the Expression of Lactate Dehydrogenase and Deletion of Pyruvate Decarboxylase Genes for the Lactic Acid Fermentation at Low pH Value", Journal of Fermentation and Bioengineering, vol. 36, No. 3, pp. 284-289, 1998.
Brambilla, L. et al., "NADH reoxidation does not control glycolytic flux during exposure of respiring *Saccharomyces cerevisiae* cultures to glucose excess", FEMS Microbiology Letters, vol. 171, pp. 133-140, 1999.
Dequin, Sylvie et al., "Mixed Lactic Acid-Alcoholic Fermentation by *Saccharomyes cerevisiae* Expressing the *Lactobacillus casei* L (+)-LDH", Bio/Technology, vol. 12, pp. 173-176, Feb. 1994.
Porro, Danilo et al., "Development of Metabolically Engineered *Saccharomyces cerevisiae* Cells for the Production of Lactic Acid", Biotechnol. Prog., vol. 11, pp. 294-298, 1995.

* cited by examiner

*Primary Examiner*—Michele K Joike
(74) *Attorney, Agent, or Firm*—Oblon, Spivak, McClelland, Maier & Neustadt, L.L.P.

(57) ABSTRACT

The invention provides a promoter that can be used in the presence of an organic acid. The promoter includes DNA with promoter activity of high osmolarity response 7 gene (HOR7 gene), glyceraldehyde 3 phosphate dehydrogenase 2 gene (TDH2 gene), heat shock protein 30 gene (HSP30), hexose transport protein 7 gene (HXT7 gene), thioredoxin peroxidase 1 gene (AHP1 gene), or membrane protein 1 associated gene gene) of yeasts.

10 Claims, 10 Drawing Sheets

PROMOTER IN THE PRESENCE OF ORGANIC ACID AND UTILIZATION THEREOF

TECHNICAL FIELD

The present invention relates to promoter DNAs in the presence of organic acids, DNA constructs, transformants, expression methods of a recombinant gene, and their uses in organic acid production methods.

BACKGROUND ART

With advances in recombinant DNA technology, techniques to obtain objective gene products have developed through expression of a foreign gene in hosts such as bacteria, fungi, animals, plants, and insects, and proliferation of the transformants. For example, culture of recombinant yeasts allows production of large amounts of objective gene products by means of fermentative production. Concerning the production of valuable organic acids such as L-lactic acid, there have been many reports of the L-lactic acid production experiments by introducing the L-lactate dehydrogenase gene into yeast *Saccharomyces cerevisiae*.

To achieve high productivity of the objective substance from recombinants, a stable high-level gene expression system must be established. The inventors have already established a system to express an L-lactate dehydrogenase gene using an original promoter function of the foreign PDC1 gene and exclude the expression of PDC1 protein that is expressed by the original foreign promoter, by linking the objective valuable gene (L-lactate dehydrogenase gene in this case) in the downstream of chromosomal PDC1 promoter and disrupting the yeast chromosomal PDC1 gene simultaneously. The inventors have disclosed in Japanese Published Unexamined Patent Application 2003-164295 that the use of this system overcomes conventional difficulties and allows stable high-level gene expression.

Although such a stable high-level gene expression system has been established, a promoter with strong expression potency is needed to further increase the productivity of recombinant products. The yeast promoters published include alcohol dehydrogenase 1 gene (ADH1) promoter (J Ferment Bioeng, 1998, Vol. 8 6(3) pp 284-289), triose phosphate isomerase gene (TPI1) promoter (FEMS Microbial Lett, 1999, Feb. Vol. 171 (2) pp 133-140), and the like.

DISCLOSURE OF INVENTION

However, the ADH1 and TPI1 promoters are not necessarily appropriate specific and strong enough for expression for the production of large amounts of organic acids such as lactic acid. In addition, they are not necessarily suitable for strong expression in the presence of an organic acid. Thus, an object of the invention is to provide promoters usable in the presence of an organic acid, DNA constructs having the promoters, transformants comprising the DNA constructs, expression methods of recombinant genes in the transformants, and production methods of organic acids using the transformants.

The inventors obtained mRNA from lactic acid-producing yeasts or yeasts growing in lactic acid-containing medium and conducted thorough gene expression analysis by a quantitative PCR method. As a result, the inventors discovered several genes that were highly expressed specifically in lactic acid-producing yeasts, and isolated those promoters. Then, to disrupt the PDC1 gene on a yeast chromosome, an expression cassette having a L-lactate dehydrogenase gene in the downstream of these promoters was integrated into the PDC1 gene locus that had previously been mapped to the chromosome, and the production of large amounts of L-lactic acids was confirmed. That is, the inventors have obtained promoters that activate the transcription of an object gene during the production of organic acids and demonstrated that these promoters virtually increased the production of L-lactic acid, and thereby achieved the invention.

Thus, the promoter that activates the transcription of operatively-associated DNA in the presence of an organic acid is useful to increase the objective gene product in the presence of an organic acid, in particular, those are useful to increase the objective product during the production of an organic acid. Therefore, such a promoter can be used to increase the production of organic acids by manipulatively associating protein genes involved in organic acid production. With the use of this promoter, recombinants transformed to produce organic acids such as lactic acid in yeasts, including *Saccharomyces*, can be obtained by genetic engineering, and such recombinants are useful as those that have high productivity of organic acids.

The present invention relates to a promoter usable in the presence of an organic acid, and the invention is provided in the following embodiments.

(1) A promoter DNA for expression in the presence of an organic acid, having the sequence set forth in any one of the following (a)-(c):

(a) a DNA consisting of the sequences set forth in any one of SEQ ID NOs: 1-6.

(b) a DNA that hybridize under stringent condition with the DNA consisting of the sequences set forth in any one of SEQ ID NOs: 1-6.

(c) a DNA carrying 1 or more bases of substitution, deletion, addition, and/or insertion in the sequences set forth in any one of SEQ ID NOs: 1-6.

(2) A fragment of the promoter DNA according to (1), being DNA as a promoter for expression in the presence of an organic acid.

(3) A promoter DNA for expression in the presence of an organic acid, having promoter activity of high osmolarity response 7 gene (HOR7 gene), glycelaldehyde 3 phosphate dehydrogenase 2 gene (TDH2 gene), heat shock protein 30 gene (HSP30), hexose transport protein 7 gene (HXT7 gene), thioredoxin peroxidase 1 gene (AHP1 gene), or membrane protein 1 associated gene (MRH1 gene) of yeast *Saccharomyces*.

(4) The promoter DNA according to any one of (1) to (3), being used for expression of DNA for organic acid production.

(5) The promoter DNA according to (4), wherein the organic acid is lactic acid.

(6) A DNA construct for gene recombination, including the promoter DNA according to any one of (1) to (3).

(7) The DNA construct according to (6), including a DNA that is operatively associated with the promoter DNA and encodes a protein involved in organic acid production.

(8) The DNA construct according to (7), wherein the protein involved in organic acid production has lactate dehydrogenase activity.

(9) The DNA construct according to (8), wherein the protein is bovine lactate dehydrogenase.

(10) The DNA construct according to anyone of (6) to (9), including a DNA for homologous recombination of yeast genes with an autoregulatory mechanism.

(11) The DNA construct according to (10), wherein the yeast gene is pyruvate decarboxylase 1 (PDC1) gene.

(12) The DNA construct of any one according to any one of (6) to (11), being plasmid or a virus vector.

(13) A transformant carrying the promoter DNA according to any one of (1) to (3).

(14) The transformant according to (13), carrying a DNA that is operatively associated with the promoter DNA and encodes a protein involved in organic acid production.

(15) The transformant according to (14), wherein the protein involved in organic acid production has lactate dehydrogenase activity.

(16) The transformant according to (14) or (15), wherein the promoter DNA according to any one of (1) to (3) and the DNA that encodes a protein involved in an organic acid production are integrated into a host chromosome.

(17) The transformant according to any one of (13) to (16), being a yeast transformant.

(18) A yeast transformant, wherein a yeast gene with an autoregulatory mechanism is disrupted by having at least part of the promoter DNA of any one according to (1) to (3) and a DNA that is operatively associated with the DNA that encodes a protein with lactate dehydrogenase activity on the chromosome.

(19) The yeast transformant according to (18), wherein the yeast gene with an autoregulatory mechanism is pyruvate decarboxylase 1 gene.

(20) The yeast transformant according to (19), wherein the protein with lactate dehydrogenase activity is bovine lactate dehydrogenase.

(21) The yeast transformant according to any one of (18) to (20), wherein the yeast belongs to *Saccharomyces*.

(22) An expression method of objective gene, using a host cell carrying the promoter DNA according to any one of (1) to (3) and a DNA that is operatively associated at the downstream region of the DNA and encodes a predetermined protein.

(23) The expression method according to (22), wherein the culture system of the host cell contains an organic acid.

(24) The expression method according to (22) or (23), wherein the host is yeast carrying a gene with an autoregulatory mechanism, which is disrupted by having at least part of the promoter DNA of any one according to (1) to (3) and a DNA that is operatively associated with the DNA that encodes proteins with lactate dehydrogenase activity on chromosome.

(25) The expression method according to (24), wherein the protein is a protein involved in organic acid production.

(26) The expression method according to (25), wherein the protein is a protein with lactate dehydrogenase activity.

(27) The production method of an organic acid using a yeast transformant having the promoter DNA according to any one of (1) to (3) and a DNA that is operatively associated at the downstream region of the DNA and encodes proteins involved in organic acid production.

(28) The production method according to (27), wherein the organic acid is lactic acid and the protein is a protein with lactate dehydrogenase activity.

(29) The production method according to any one of (27) or (28), wherein the DNA is retained on yeast chromosome and pyruvate decarboxylase 1 gene is disrupted by at least a part of the DNA.

(30) A DNA having promoter activity according to any one of the following (a)-(c):

(a) a DNA consisting of the sequence set forth in any one of SEQ ID NOs: 1-6.

(b) a DNA that hybridize DNA consisting of a sequence set forth in any one of SEQ ID NOs: 1-6 under stringent condition.

(c) a DNA carrying 1 or more bases of substitution, deletion, addition, and/or insertion in the sequence set forth in any one of SEQ ID NOs: 1-6.

(31) A fragment of the DNA according to (29), having promoter activity.

BEST MODES FOR CARRYING OUT THE INVENTION

Figure 1:
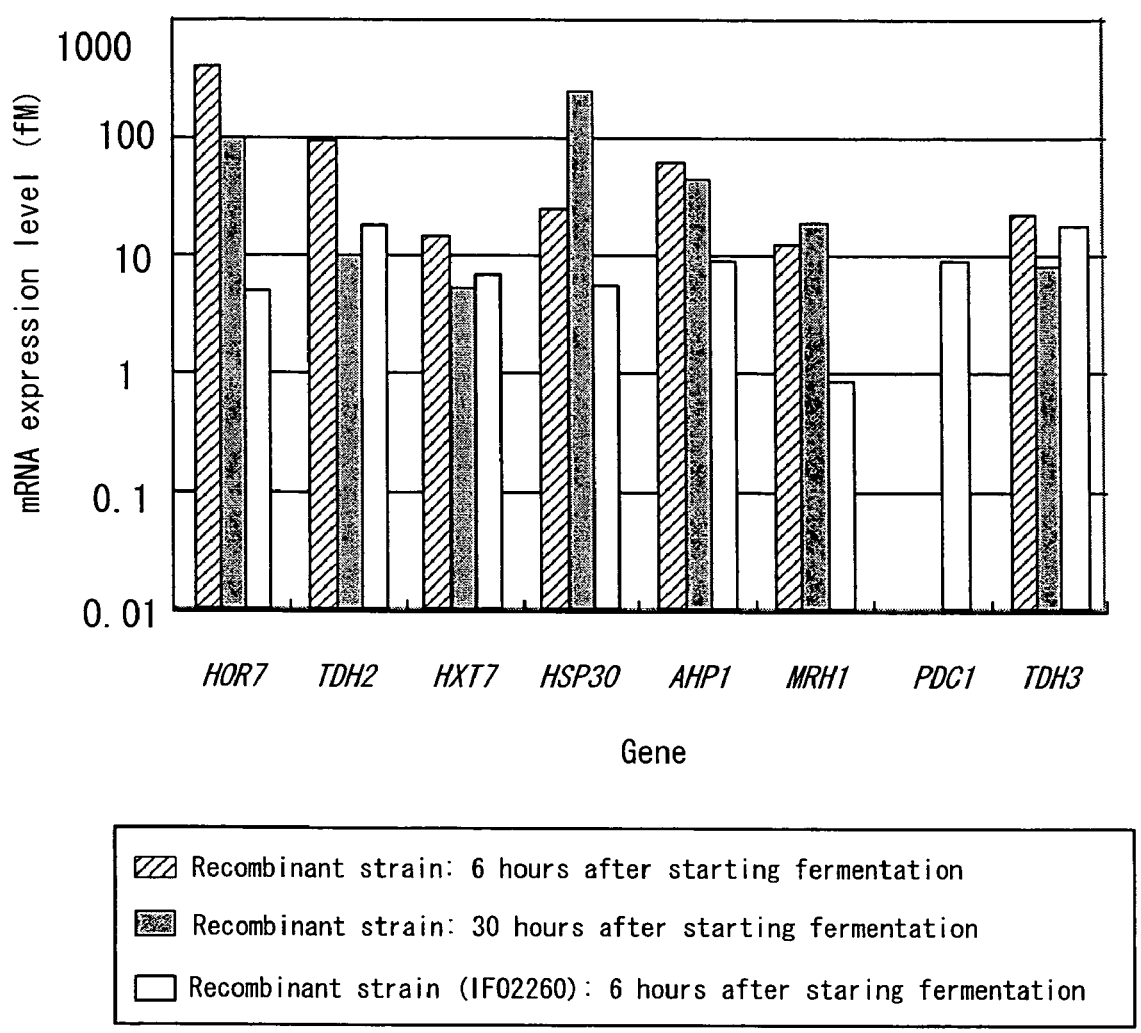
FIG. 1 is a graph showing mRNA expression levels during lactic acid fermentation, measured by quantitative PCR.

The promoter of the invention activates or enhances expression in the presence of an organic acid. More specifically, the promoter of the invention activates the expression of DNA that encodes a protein, which is operatively associated to the promoter that is activated only in the presence of an organic acid or enhanced more strongly than in the absence of organic acid, or have promoter activity that is enhanced with an increase in organic acid level (hereinafter, the activity is referred to as the promoter activity). "Operatively associated," as used herein, refers to the linkage that keeps the expression of DNA encoding the linked protein under the influence or control of these promoters. The "Organic acid" refers to an acidic organic compound, and the acid group of the organic acid is preferably carboxylic acid. In addition, organic acids contain organic salts besides free acids. Such organic acids include, specifically, lactic acid, butyric acid, acetic acid, pyruvic acid, succinic acid, formic acid, malic acid, citric acid, malonic acid, propionic acid, ascorbic acid, and adipic acid; lactic acid is preferable. There are L-, D-, and DL-lactic acids; all of them are included. "In the presence of organic acid" means that the presence of organic acid in the environment where a host carrying promoter DNA of the invention grows, and the organic acid may be those produced by the host carrying the promoter of the invention and/or those supplied from sources other than the host, such as a medium. The organic acid level in the culture system is not specifically determined, but may be within the range in which the coding DNA that is operatively associated with the promoter of the invention is expressed or enhanced.

The promoter DNA of the invention that activate transcription in the presence of an organic acid includes those with promoter activity, having the sequence set forth in any one of SEQ ID NOs: 1-6. Besides DNA consisting of any of these sequences, the promoter DNA of the invention includes those that hybridize with DNA having the sequence set forth in the any one of above sequences and have the promoter activity. Such DNA can be obtained by common hybridization technique (Southern, EM., J Mol Biol, 1975, 98, 503) using the DNA having the sequence set forth in any one of SEQ ID NOs: 1-6 or part of them as a probe. In addition, the DNA can be synthesized by PCR technique (Saiki RK. Science, 1985, 230, 1350, Saiki RK. et al., Science, 1988, 239, 487) using oligonucleotides that specifically hybridize to the DNA having the sequence set forth in any one of SEQ ID NOs: 1-6 as primers. DNA highly homologous to those having the sequence set forth in any one of SEQ ID NOs: 1-6 can be isolated by the hybridization or PCR. For isolation, hybridization under stringent conditions is preferred. The stringent condition refer to a hybridization condition in the presence of 50% formamide and at a hybridization temperature of 37° C. or those with the same stringency. More stringent condition allow isolation of DNA having higher homology. Such hybridization condition include, for example, those in the presence of 50% formamide at a hybridization temperature of about 42° C., and higher stringent conditions include those in the presence of 50% for amide at a hybridization temperature of about 65° C.

In addition, the promoter DNA of the invention may have the sequence set forth in any one of SEQ ID NOs: 1-6, with 1 or more bases of substitution, deletion, addition, and/or insertion but the promoter activities maintained. Such DNAs can be obtained by the above-mentioned hybridization and PCR techniques and the like, and mutations can be artificially introduced into the sequences set forth in any one of SEQ ID NOs: 1-6 by site-directed mutagenesis (Kramer W & Fritz H J., Method Enzymol, 1987, 154, 350).

The homology of the isolated DNA with the sequence set forth in SEQ ID NOs: 1-6 is preferably 70% and above, more preferably 80% and above, and most preferably 90% and above. The DNA sequence homology can be determined by a BLAST gene analysis program and the like. DNA sequence homology can be determined by BLAST (on the Internet at blast.genome.ad.jp) and FASTA (on the Internet at fast-a.genome.ad.jp/SIT/FASTA.html) gene analysis programs and the like.

The DNA consisting of the sequence set forth in SEQ ID NOs: 1-6 has each been obtained as DNA fragments with promoter activity of high osmolarity response 7 gene (HOR7 gene), glycelaldehyde-3-phosphate dehydrogenase 2 gene (TDH2 gene), hexose transport protein 7 gene (HXT7 gene), and heat shock protein 30 gene (HSP30 gene), thioredoxin peroxidase 1 gene (AHP1 gene), and membrane protein 1 associated gene (MRH1 gene) of yeast *Saccharomyces cerevisiae*. Thus, the promoter DNA of the invention may be DNA with the promoter activity of yeast or *Saccharomyces* yeast, or DNA with the promoter activity, which share homology with the promoter region. Such DNA can be obtained from yeasts by a hybridization technique using a probe carrying at least part of the sequence set forth in any one of SEQ ID NOs: 1-6 and a PCR technique using oligonucleotides probes that hybridize the sequence. In addition, DNA that hybridize under the above-mentioned stringent condition can be selected.

The promoter DNA of the invention may be DNA fragment of the DNA in various forms described herein, as long as the DNA fragment have the promoter activities.

Each DNA having the sequence set forth in SEQ ID NOs: 1-6 was selected through screening during lactic acid fermentation under neutralizing conditions (pH4.0-8.0) in lactic acid-producing yeasts. In the screening, genes were selected, which showed high-level expression in the quantification by quantitative PCR using cDNA obtained from mRNA collected at the predetermined time points after starting lactic acid fermentation using lactic acid-producing yeasts under the above-mentioned neutralizing conditions. Such screening allows extraction of genes that are highly expressed during lactic acid production (in the presence of lactic acid) in lactic acid-producing yeasts, and thus can obtain promoters showing high-level expression during lactic acid production (in the presence of lactic acid) by isolating the promoters of the genes.

The Promoter obtained by the screening can also be regarded as lactic acid-inducible promoters that induce gene expression by lactic acid. Thus, operatively associating DNA that encodes a protein with enzymatic activity involved in lactic acid production, such as lactate dehydrogenase, to the promoters is highly expected to produce useful transformants of lactic acid-producing yeasts whose lactic acid production is not suppressed or further enhanced by increased lactic acid production.

Whether or not the obtained DNA has the promoter activity can be confirmed by a reporter assay using a reporter gene known by those skilled in the art. Any known genes may be used as a reporter gene without limitation; for example, chloramphenicol acetyl transferase (CAT), β-galactosidase (LacZ), luciferase (LUC), β-glucuronidase, green fluorescent protein (GFP) genes, and the like can be mentioned. In addition, the presence of the promoter activity can be confirmed using a gene whose expression can be confirmed by measuring the amounts of protein encoded by the gene and activity (e.g., amounts of metabolites) of the protein (enzyme). Furthermore, the promoter activity can also be confirmed by measuring transcripts using Northern hybridization and quantitative PCR methods for mRNA obtained by gene expression. Since the promoter activity activates or enhances expression in the presence of an organic acid, culture systems including organic acids or hosts that produce organic acids are preferably used to confirm the promoter activity.

The prompter DNA of the invention may be a genomic DNA or a chemically-synthesized DNA.

The invention also provides a DNA construct for recombinant including the promoter DNA of the invention. Plasmids (DNA), viruses (DNA) bacteriophages (DNA), retrotransposons (DNA), and artificial chromosomes (YAC, PAC, BAC, MAC, and others), without particular limitation, can be selected for the DNA construct for recombinant, and they take forms as a vector according to the mode of introducing a foreign gene (extrachromosomal and intrachromosomal) and kinds of host cells. Thus, the DNA construct can incorporate DNA besides the promoter DNA by taking one of these forms as a vector. Preferably the DNA construct take a form as a plasmid vector or a virus vector. In addition, preferable prokaryotic cells, eukaryotic cells, animal cells, and plant cell vectors are well known in the relevant fields. These DNA constructs can be retained within cytoplasm or extrachromosomally in host cells, or integrated into and retained in the host chromosome.

The DNA construct carries DNA that encodes an intended protein (hereinafter also referred to as code DNA), which is operatively associated to the promoter DNA. The code DNA may include not only cDNAs but also DNAsequences that are transcribed but not translated. Although proteins are not specifically limited, the code DNA may be those for the production of an organic acid such as lactic acid, i.e., those that encode proteins having enzyme activities involved in organic acid production. Operative association of such DNA that encodes the protein to the promoter is expected to allow synergically enhanced organic acid production. Such enzymes include L-lactate dehydrogenases and D-lactate dehydrogenases for lactic acid production, pyruvate kinase for pyruvic acid production, pyruvate oxidase for acetic acid production, succinyl-CoA synthetase for succinic acid production, fumarate hydratase for malic acid production, and citrate synthase for citric acid production, and the like.

There are various homologs of lactate dehydrogenase (LDH) within a living body and according to species. The lactate dehydrogenases used in the invention include chemically-synthesized or genetically-engineered artificial LDHs as well as naturally-occurring ones. Preferably, LDH is derived from prokaryotes such as *Lactobacillus* or eukaryotic microorganisms such as fungi, and more preferably higher eukaryotes such as plants, animals, and insects, and most preferably higher eukaryotes including mammals like cattle. Bovine LDH (L-LDH) is most preferable. For example, bovine LDH includes the protein carrying the amino acid sequence set forth in SEQ ID NO: 8. In addition, the DNAs encoding the LDH include the DNA carrying the sequence set forth in SEQ ID NO: 7. Furthermore, LDHs in the invention includes the homologs of these LDHs. The LDH homologs include protein with LDH activity, which carry 1 or more amino acids of substitution, deletion, insertion, and/or addition in the amino acid sequences of naturally-occurring LDHs, and protein with LDH activity, which share at least 70%, and preferably 80% or more, homology with the amino acid sequence of naturally-occurring LDH.

The DNA construct can have a DNAsequence for homologous recombination to integrate the promoter DNA and code DNA into the host chromosome by homologous recombination. Inclusion of the DNA allows integration of the DNA into the desired locus on the host chromosome and disruption of the desired gene simultaneously. The DNAsequences for homologous recombination are those homologous to the target locus to introduce the DNA or its flanking region on the host chromosome. The DNAsequences for homologous recombination have one sequence homologous to one target gene or at least one flanking region, and more preferably, have a sequence homologous to at least two regions of the target gene or its flanking regions. For example, the DNAsequences each homologous to the upstream side and downstream side of the target locus on chromosome are determined as two DNAsequences for homologous recombination, and the promoter DNA or code DNA is preferably linked between the DNAsequence for homologous recombination.

In case of the introduction of the DNA into the host chromosome by homologous recombination, the DNA construct of the invention allows the control of the expression of code DNA under the regulation of the promoter DNA by selecting appropriate DNA for homologous recombination and inserting the DNA promoter and code DNA into the desired locus on the host chromosome. DNA for homologous recombination which is selected to achieve such integration into a chromosome, is well known to those skilled in the art, therefore, they can select appropriate DNA for homologous recombination according to need, and prepare DNA constructs for homologous recombination.

If a host chromosome intrinsically carries the promoter DNAselection of appropriate DNA for homologous recombination also allows the integration of the promoter DNA and code DNA into their original locus of the promoter DNA on the host chromosome. In this way, instead of the original regulation of intrinsic code DNA by the promoter on chromosome, the promoter can control foreign code DNA. As a result, the expression of intrinsic code DNA that is activated under normal circumstances is suppressed, while the promoter DNA can activate the expression of extrinsic code DNA on the original locus of the promoter DNA on a chromosome. Such a DNA construct having the promoter and at least a part of the intrinsic structure gene, which is controlled by the promoter, as DNA for homologous recombination can be integrated into the host chromosome.

Selection of DNA for homologous recombination allows integration of this promoter DNA into chromosome and disruption of the desired gene on the host chromosome simultaneously. The gene to be disrupted is preferably those having an autoregulatory mechanism that will be described later. For example, when organic acids are produced in yeasts, such as *Saccharomyces* yeast, using DNA that encodes a protein involved in organic acid production, pyruvate decarboxylase gene (particularly, pyruvate decarboxylase 1 gene) is preferably disrupted. This is because the promoter of pyruvate decarboxylase 1 gene is strong and has an autoregulatory mechanism as described later. Integration of the gene for disruption can suppress the expression of pyruvate decarboxylase gene and express the protein encoded by foreign DNA. In addition, since the expression of foreign code DNA is activated by the promoter in the presence of an organic acid, increased organic acid production by expressed proteins further enhance the expression of the foreign code DNA.

Particularly, when lactic acid is produced using DNA that encodes lactate dehydrogenase, the above-mentioned mode of disruption is more effective. This is because the pyruvate decarboxylase 1 gene works competitively with lactate dehydrogenase for pyruvic acid, a substrate of lactate dehydrogenase. Disruption of the gene suppresses the expression of pyruvate decarboxylase and allows the expression of lactate dehydrogenase, and simultaneously, expression of lactate dehydrogenase is activated by the promoter DNA in the presence of an organic acid (i.e., lactic acid); thus, the production of lactic acid is expected to be further enhanced. To achieve such integration into a chromosome, the DNA construct may include, for example, part of the structure gene of pyruvate decarboxylase or its flanking sequence (a flanking sequence around a start codon, a upstream region sequence of a start codon (including the promoter of this structure gene), a sequence within the structure gene, and the like) or DNAsequences homologous to the further upstream region and/or downstream side of the gene on chromosome. Using *Saccharomyces* (particularly, *Saccharomyces cerevisiae*) as a host, DNA construct preferably target pyruvate decarboxylase 1 gene in this host.

The promoter of pyruvate decarboxylase gene is strong, and thus can be used in combination with the promoter DNA. More specifically, DNA constructs usable include those for homologous recombination to introduce DNA that encodes a protein with lactate dehydrogenase activity in place of the structure gene, which is controlled by the gene promoter under normal circumstances, into the internal region of pyruvate decarboxylase gene (preferably, pyruvate decarboxylase 1 gene) on a yeast chromosome, and those for homologous recombination to introduce DNA that encodes a protein with lactate dehydrogenase activity in place of the structure gene, which is controlled by the DNA promoter under normal circumstances, into the internal region of the DNA promoter on a yeast chromosome. More effective lactic acid production is expected by enhancing effects of both PDC gene (preferably, PDC1 gene) promoter and the promoter DNA on the expression, and by suppression of pyruvate decarboxylase gene expression by disruption of the PDC (preferably, PDC1) structure gene. In addition, even if the PDC1 gene is disrupted, growth capacity of yeasts is maintained due to the alternative biosynthesis of pyruvate decarboxylase by other PDC5 genes. Such a DNA construct may contain DNA with PDC1 promoter activity, which fulfills functions of both promoter DNA and DNA for homologous recombination. In addition to DNA having the sequence set forth in SEQ ID NO: 9, DNA that hybridizes with the DNA under stringent conditions and DNA having the sequence carrying 1 or more bases of substitution, deletion, addition, and/or insertion, can be used as PDC1 promoter DNA Such DNA can be isolated in the same manner as this promoter DNA.

The PDC1 gene, as already disclosed by the inventor, has an autoregulatory mechanism (Japanese Published Unexamined Patent Application No. 2003-164295). A single creature has multiple genes with the same function, and under ordinary circumstances, at least one of them is expressed, while the others are suppressed. The autoregulatory mechanism refers to compensatory gene expression: only when a gene that is expressed under ordinary circumstances is disrupted and becomes nonfunctional, the remaining genes are expressed to fulfill its function. Because this mechanism exists, even if yeast PDC1 gene, for example, is disrupted, PDC5 gene is activated and ethanol production function of yeasts is maintained to fulfill the physiological function. Disruption of a gene with such an autoregulatory mechanism allows survival of the organism and maintains the growth function, resulting in the effective production of objective substance while maintaining the growth of transformants carrying the foreign DNA.

If needed, terminator, as well as cis-elements such as enhancer, splicing signal, poly A addition signal, selection marker, and ribosome binding sequence (SD sequence), may be linked to the DNA construct. Examples of the selection marker include various known selection markers such as drug resistance gene and auxotrophic gene, such as, for example, ampicillin resistance gene, kanamycin resistance G418 gene, hygromycin resistance gene, bleomycin resistance gene, neomycin resistance gene, dihydrofolate reductase gene, chloramphenicol resistance gene, and cycloheximide resistance genes, and the like.

This DNA constructs can be introduced into appropriate host cells by various proper techniques, including transformation, transfection, conjugation, protoplast fusion, electroporation, lipofection, lithium acetate, particle gun, calcium phosphate precipitation, *Agrobacterium*, PEG, direct microinjection, and the like. After introduction of the DNA construct, recipient cells are cultured on a selection medium.

Examples of host cells include bacteria such as *Escherichia coli* and *Bacillus subtilis*, *Saccharomyces* yeasts such as *Saccharomyces cerevisiae* and *Saccharomyces pombe*, yeasts such as *Pichia pastoris*, insect cells such as sf9 and sf21, animal cells such as COS cells and Chinese hamster ovary (CHO) cells, plant cells of sweet potato and tobacco, and the like. Preferably, microorganisms that cause alcohol fermentation, such as yeast, or acid resistance microorganisms such as *Saccharomyces* yeasts like *Saccharomyces cerevisiae*, for example, are used. More specifically, *Saccharomyces cerevisiae* IFo2260 strain and YPH strain are exemplified.

Whether or not this DNA constructs are introduced into a host, or are introduced into the desired locus on chromosome can be confirmed by the PCR method and Southern hybridization method. For example, confirmation can be made by conducting PCR using integration site-specific primers on DNA prepared from transformants and electrophoretically detecting the expected band of PCR products. Alternatively, PCR using fluorescent dye-labeled primers can be used for confirmation. These methods are well known to those skilled in the art.

The components of the DNA construct in a transformant, including this promoter DNA, code DNA, and others, exist on chromosome or extrachromosomal genetic element (including artificial chromosome). When a DNA construct for homologous recombination that can achieve homologous recombination is introduced, transformant carrying code DNA operatively associated with the promoter and the DNA at the desired locus on the host chromosome can be obtained.

In one preferable embodiment of the transformant obtained by homologous recombination with a host chromosome, code DNA is operatively associated to the promoter DNA on a chromosomal locus where the promoter DNA is inherently located. In the transformant, since the expression of code DNA is activated by the promoter DNA in the presence of an organic acid, objective products are effectively obtained in the presence of an organic acid. In this embodiment, code DNA preferably encodes a protein with lactate dehydrogenase activity. The transformant produces lactic acids by the lactate dehydrogenase activity, and the lactic acid production further enhances the expression of the enzyme activity and increases the lactic acid production.

In another preferable embodiment of the transformant of the invention, a gene with an autoregulatory mechanism is disrupted on the host (e.g., yeast) chromosome, and simultaneously, code DNA is operatively associated with this promoter DNA and the DNA in place of the promoter of the gene. In the transformant, code DNA can be expressed specifically by these DNA without producing lethal functional damages to the host. When DNA that encodes a protein with lactate dehydrogenase activity is used as code DNA, lactic acid can be produced while inhibiting the damages on the growth of the host.

In another preferable embodiment of the invention, PDC1 gene on a host (e.g., yeast) chromosome is disrupted, and simultaneously, code DNA is operatively associated with this promoter DNA and the DNA in place of the promoter of the gene. In the transformant, particularly when code DNA encoding a protein with lactate dehydrogenase activity is used, lactate dehydrogenase can be expressed by this promoter DNA while suppressing the expression of competitive pyruvate decarboxylase; thus, a transformant suitable for lactic acid production can be obtained. As previously stated, even when the PDC1 gene is disrupted, growth capacity and others of the host are maintained due to the autoregulatory mechanism of the gene.

In another preferable embodiment of the transformant, code DNA is operatively associated to this promoter DNA and the DNA on the host chromosome (e.g., one of the above-mentioned three preferable embodiments or combinations of them), and simultaneously, code DNA is operatively associated to the PDC1 promoter DNA and the DNA on the host chromosome or extrachromosomally the host. In this embodiment, if all code DNA encodes a protein with enzyme activity involved in the biosynthesis of organic acids such as lactic acid, the expression of biosynthetic enzyme of organic acids is constitutively activated by the PDC1 promoter, and the expression of biosynthetic enzyme of organic acids is organic acid-inductively activated by the promoter DNA; thus, highly efficient organic acid production can be expected. Particularly, in this embodiment, intrinsic DNA on a chromosome is preferably used as PDC1 promoter. This allows stable expression from PDC1 promoter.

The preferable host of the transformant is yeast, particularly *Saccharomyces* yeast, and more preferably *Saccharomyces cerevisiae*. In addition, code DNA is preferably those encoding proteins with lactate dehydrogenase activity, and more preferably, DNA encoding bovine lactate dehydrogenase.

In the invention, it is important to express code DNA by this promoter DNA on a host chromosome. In particular, to obtain a transformant that do not produce organic acids under normal circumstances or increase organic acid production above the original production level, methods by YEP type plasmid vector using 2 μm DNA are often used, but in this case, problems in the retention of the code DNA have been reported. However, in the invention, expression activity was found too high to consider that this resulted from high DNA retention alone. Thus, according to the invention, a stable and unexpectedly high-level gene expression system of code DNA can be constructed with the use of the promoter DNA on a chromosome in the presence of an organic acid by activating expression of code DNA that is operatively associated to the DNA. In addition, when code DNA encodes a protein with enzyme activity, which is involved in organic acid biosynthesis, such as lactate dehydrogenase, the final product (i.e., organic acid) of code DNA, whose expression is activated by the promoter DNA, is expected to further activate the expression of code DNA by the promoter DNA. That is, synergistically and consecutive biosynthesis of proteins and enhanced biosynthesis of the final products are expected.

In addition, when DNA that encodes a protein with lactate dehydrogenase activity is used as code DNA, disruption of PDC1 gene by introduction of the promoter DNA and code DNA into the host chromosome can provide effective enhancement of lactic acid production via suppressive effects of the PDC1 gene disruption on the expression of pyruvate decarboxylase, as well as the above-mentioned effects.

In introducing DNA that encodes lactate dehydrogenase at the downstream of the promoter DNA of the invention, in order to increase the lactic acid production, transformants carrying multiple these gene-integration fragments in the chromosome can be made. In this case, 2 or more kinds of the promoter can be used in combination, as well as one. In the embodiment using 2 or more kinds of the promoter in combination, code DNA is linked to each promoter to express lactate dehydrogenase from each promoter. For example, a transformant can be prepared, which is introduced with 1 or more kinds of gene-integration fragments that was constructed by linking 2 or more kinds of promoter DNA of the promoter DNA each to DNA that encodes a protein with lactate dehydrogenase activity. In a more specific example, a transformant can be obtained, which expresses proteins with lactate dehydrogenase activity from HOR7 and TDH2 promoters in combination within the same transformant by introducing a gene-integration fragment linked with code DNA at the downstream region of HOR7 promoter and a gene-integration fragment linked with code DNA at the downstream region of TDH2 promoter. The promoter is not limited thereto; for example, other promoters such as PDH1 promoter can be used in combination.

Although not limiting the invention, the above-mentioned fact that unexpectedly larger amounts of lactic acid production was achieved by activating the expression of DNA that encodes a protein with lactate dehydrogenase activity on a host chromosome with the use of endogenous promoters (the DNA promoter and PDC1 promoter) on the chromosome is considered to have mainly resulted from the expression of DNA that encodes a protein with lactate dehydrogenase activity in place of a structure gene that is controlled by these promoters under ordinary circumstances on the chromosome loci where they originally resided. That is, alternative expression of other lactate dehydrogenase with the use of the promoter on these promoter loci of chromosome, or alternative expression of lactate dehydrogenase with the use of other promoter in place of the promoter and structure gene is considered important. In addition to these causes, regarding PDC1 promoter, the fact that PDC1 is a strong constitutive promoter and the promoter of a gene with an autoregulatory mechanism is considered to contribute to increased amounts of lactic acid production, and regarding this promoter DNA, the fact that the promoter is an inducible one that activates expression in the presence of an organic acid (lactic acid) is considered to contribute to an increase in lactic acid production.

Culturing of the transformant obtained by introducing the DNA construct allows production of proteins, expressed by a foreign gene, into the culture. Since this expression method enhances the expression of code DNA in the presence of an organic acid, addition of an organic acid to the culture system etc., can enhance the production of useful proteins. When code DNA encodes a protein involved in organic acid production, organic acid production by enhanced expression of the code DNA further enhances its expression. Here, even if code DNA encodes a protein involved in organic acid production, an organic acid may be added to the culture system from outside. When the protein is an enzyme involved in the biosynthesis of an organic acid, such as lactate dehydrogenase, an organic acid such as lactic acid is produced into the culture system. The organic acid can be obtained by performing the isolation process of organic acid from the culture system. The culture in the invention includes cultured cells or fungus bodies, cells, or fungus fractures, as well as culture supernatants.

In culturing the transformant of the invention, culture conditions can be selected according to the kind of the transformant. Such culture conditions are well known to those skilled in the art. In the production of an organic acid such as lactic acid, the product (lactic acid, etc.) is neutralized or lactic acid is sequentially removed if needed. Both natural and synthetic media can be used as media to culture a transformant that is obtained using microorganisms, including E. coli and yeasts, as hosts, as long as the media contain carbon sources, nitrogen sources, and inorganic salts that the bacteria can assimilate, and transformants are effectively cultured. Examples of carbon sources include glucose, fructose, sucrose, starch, carbohydrate of cellulose and others, organic acids such as acetic acid and propionic acid, and alcohols such as ethanol and propanol. Examples of nitrogen sources include inorganic acids such as ammonia, ammonium chloride, ammonium sulfate, ammonium acetate, and ammonium phosphate, organic acids such as ammonium salt, or other nitrogenous compounds, peptone, meat extract, corn steep liquor, and the like. Examples of inorganic substances include monobasic potassium phosphate, magnesium phosphate, magnesium sulfate, sodium chloride, ferrous sulfate, manganese sulfate, copper sulfate, and calcium carbonate.

Culturing is normally conducted at 30° C. for 6-24 hours under aerobic conditions such as a shaking culture or aeration-agitation culture. Preferably, pH is maintained at 2.0-6.0 during the culture period. The pH may be adjusted using inorganic or organic acids, alkaline solution, and the like. If needed, antibiotics such as ampicillin and tetracycline may be added to the medium during the culture.

After completing the culture, to isolate a gene product from the culture, a common lactic acid purification method can be used. For example, when produced within a transformed cell, to separate a gene product from the cell, bacteria are destroyed using a common procedure, including ultrasonic destruction treatment, triturator, and pressure fracturing. In this case, protease is added if needed. In addition, when a gene product is produced in a culture supernatant, solid content is removed from the solution by filtration and centrifugation.

Lactic acid can be purified from these crude extract fractions using various known purification and separation methods. In addition, if needed, the crude extract fractions and their purified products may be esterified to obtain various lactic acid derivatives.

Embodiment 1

Hereinafter, specific embodiments of the invention will be described, however, the invention is not limited to them but may be applied to various embodiments without departing from the scope of the invention.

(Expression Analysis by Quantitative PCR Method)

Lactic acid fermentation was performed under neutralizing conditions (pH4.0-8.0) using recombinant yeasts of Japanese Published Unexamined Patent Application No. 2003-259878 (Japanese Patent Application No. 2002-65879) as recombinant yeasts with lactic acid production ability, and bacteria at 6 and 30 hours after starting fermentation were collected for RNA preparation. RNeasy Mini kit (Qiagen) was used for RNA extraction. cDNA was synthesized from obtained RNA using the First Strand cDNA Synthesis Kit (Roche Diagnostics). The recombinant yeasts used, tryptophan synthesis-lacking yeast IFO2260 strain (a strain registered to the Institute of Fermentation), were cultured in 10 mL of YPD medium at 30° C. to logarithmic growth phase, and the yeasts are collected and washed with TE buffer, and then 0.5 mL of TE buffer and 0.5 mL of lithium acetate were added. After the shaking culture at 30° C., pBTrp-PDC1-LDHKCB vector to be described later, was digested with ApaI and SacI restriction enzymes (TAKARA), and added, and the resulting colonies were cultured in a tryptophan selection medium, and those with stable culture on a tryptophan selection medium can be obtained as strains whose stable tryptophan synthetic ability and integration of the DNA fragment into the predetermined locus on a chromosome are confirmed.

Expression analysis was performed with a mixture of the above-described sample, primers for the target gene, and the Light Cycler DNA Master SYBR Green I (Roche Diagnostics) using a quantitative PCR analysis instrument, the Light Cycler (Roche Diagnostics). The details follow the attached protocol. In addition, quantities of gene fragments (4 fM, 20 fM, and 100 fM) were each determined in the same manner, and was used as a control to determine the expression levels.

In total, expression of 28 genes was analyzed. Among them, concerning 6 candidate promoters with high-level expression, whose effective expression was finally confirmed, the primer sequences used and the Tm values in the analysis by the Light Cycler are shown. Also, PDC1 gene promoter and TDH3 gene promoter were analyzed as control promoters with high-level expression. Similarly, the primer sequences and the Tm values of these control promoters are shown.

<Primers to confirm the expression of HOR7 gene> Tm value: 60° C.

5'-CGT CGC CTT CAC TGG TTT AG-3' (SEQ ID NO: 10)

5'-CAA AAA GGC CAA AGC ACC AG-3' (SEQ ID NO: 11)

<Primers to confirm the expression of TDH2 gene> Tm value: 57° C.

5'-CAA GGT AAG TTG ACC GGT ATG-3' (SEQ ID NO: 12)

5'-GAT GGA AGA GTT AGA GTC ACC C-3' (SEQ ID NO: 13)

<Primers to confirm the expression of HXT7 gene> Tm value: 57° C.

5'-TCA TGG GCT GTT TGG TCT TC-3' (SEQ ID NO: 14)

5'-AGC GTC GTA GTT GGC ACC TC-3' (SEQ ID NO: 15)

<Primers to confirm the expression of HSP30 gene> Tm value: 57° C.

5'-AAT TGC AGT CAG CCG TGA TG-3' (SEQ ID NO: 16)

5'-TCG ACA GCT TGC TCT GCT TC-3' (SEQ ID NO: 17)

<Primers to confirm the expression of AHP1 gene> Tm value: 60° C.

5'-AAC CAA GCG TGG GCT AAG AG-3' (SEQ ID NO: 18)

5'-GGT TTC CTT GGC AGC GTA AG-3' (SEQ ID NO: 19)

<Primers to confirm the expression of MRH1 gene> Tm value: 57° C.

5'-GCT GCC TGT GTT CAC TCC AC-3' (SEQ ID NO: 20)

5'-TGG CTG CAA AAC GTT ACC AC-3' (SEQ ID NO: 21)

Primers to confirm the expression of PDC1 gene> Tm value: 60° C.

5'-CAA CGA ATT GAA CGC TGC TTA C-3' (SEQ ID NO: 22)

5'-ATT CAA CGG CTT CCT TAA CTT CTG-3' (SEQ ID NO: 23)

Primers to confirm the expression of TDH3 gene> Tm value: 7° C.

5'-GTT TTC AAG GAA TTA GAC ACT GC-3' (SEQ ID NO: 24)

5'-CAA CAG TCT TTT GAG TAG CAG TC-3' (SEQ ID NO: 25)

As a result of quantitative PCR gene promoter, HOR7 gene promoter, TDH2 gene promoter, HXT7 gene promoter, HSP30 gene promoter, AHP1 gene promoter, and MRH1 gene promoter were selected. These genes in lactic acid-producing yeasts showed higher expression than the PDC1 and TDH3 genes. These results are shown in FIG. 1. In addition, the expression levels of all these genes were higher than those of non-recombinant strains. The above results demonstrated that the expression of these genes was activated by the promoter whose expression was induced in the presence of an organic acid.

Embodiment 2

Isolation and Sequencing of Promoters

Six gene promoters (HOR7, TDH2, HXT7, HSP30, AHP1, and MRH1 gene promoters) were selected as the candidate high-level expression promoters, which showed effective expression in the embodiment 1, and these gene fragments were cloned. Also, the PDC1 gene promoter and TDH3 gene promoter, known as high-level expression promoters, were obtained as the controls to the examine promoters.

A gene source to obtain promoters was isolated by a PCR amplification method using genomic DNA of yeast IFO2260 strain (a yeast strain registered to the Institute of Fermentation) as a template. This strain was cultured overnight in 2 mL of YPD medium, and genomic DNA was prepared using genomic DNA preparation kit the GenToRukun™ for yeast (TAKARA BIO INC.). DNA concentrations of the prepared genomic DNA were measured by spectrophotometer, the Urtro spec 3000 (Amersham Pharmacia Biotech).

The KOD plus DNA polymerase (TOYOBO) to have high accuracy of amplified fragments was used as an amplification enzyme for PCR reaction. DNA amplification was performed by a PCR amplifying instrument, the Gene Amp PCR system 9700 (PE Applied Biosystems), in total 50 μL of reaction mixture containing 50 ng of genomic DNA prepared from the yeast IFO2260 strain, 50 μmol×2 primer DNAs, 5 μL of 10 times concentrated KOD enzyme reaction buffer, 2 μL of 25 mM MgSO$_4$, 5 μL of 2 mM dNTP mixture, and 1.0 unit of the KOD plus DNA polymerase. The reaction conditions of the PCR amplifying instrument were: heat treatment at 96° C. for 2 min, followed by 25 cycles (1 cycle of 3 temperatures: 96° C. for 30 min, 53° C. for 30 sec, and 72° C. for 60 sec), and finally incubation at 4° C. 5 μL of this reaction sample was electrophoresed on 1% TBE agarose gel (containing 0.5 μg/mL ethidium bromide), and DNA band was detected on this gel by ultraviolet irradiation (Funakoshi) at 254 nm to confirm gene amplification.

Primer sequences are as follows:

<Primers to Amplify HOR7 Gene Promoter>

HOR7P-U (35 mer; Tm value: 72.6° C.; restriction enzyme NotI site was added to the terminus.)
5'-ATA TAT GCG GCC GCT CGC AGC CAC GGG TCA ACC CG-3' (SEQ ID NO: 26)

HOR7P-D (41 mer; Tm value: 53.7° C.; restriction enzyme SpeI site was added to the terminus.)
5'-ATA TAT ACT AGT TTT TAT TAT TAG TCT TTT TTT TTT TTG AC-3' (SEQ ID NO: 27)

<Primers to Amplify TDH2 Gene Promoter>

TDH2P-U (39 mer; Tm value: 67.1° C.; restriction enzyme NotI site was added to the terminus.)
5'-ATA TAT GCG GCC GCT TGA CGG GTA TTC TGA GCA TCT TAC-3' (SEQ ID NO: 28)

TDH2P-D (38 mer; Tm value: 56.5° C.; restriction enzyme SpeI site was added to the terminus.)
5'-TAT ATA CTA GTT TGT TTT GTT TGT TTG TGT GAT GAA TT-3' (SEQ ID NO: 29)<

Primers to Amplify HXT7 Gene Promoter>

HXT7P-U (33 mer; Tm value: 68.4° C.; restriction enzyme NotI site was added to the terminus.)
5'-ATA TAT GCG GCC GCC CTG CTA AAC ACG CCC TAC-3' (SEQ ID NO: 30)

HXT7P-D (40 mer; Tm value: 52.5° C.; restriction enzyme SpeI site was added to the terminus.)
5'-ATA TAT ACT AGT TTT TGA TTA AAA TTA AAA AAA CTT TTT G-3' (SEQ ID NO: 31)<

Primers to Amplify HSP30 Gene Promoter>

HSP30P-U (34 mer; Tm value: 64.5° C.; restriction enzyme NotI site was added to the terminus.)
5'-ATA TAT GCG GCC GCT GAA TAC GTC CTG TCA ATT C-3' (SEQ ID NO: 32)

HSP30P-D (36 mer; Tm value: 54.0° C.; restriction enzyme SpeI site was added to the terminus.)
5'-ATA TAT ACT AGT TGA AAT TTG TTG TTT TTA GTA ATC-3' (SEQ ID NO: 33)<

Primers to Amplify AHP1 Gene Promoter>

AHP1P-U (35 mer; Tm value: 65.5° C.; restriction enzyme NotI site was added to the terminus.)
5'-ATA TAT GCG GCC GCA TCC GAA TTC AAT GTA GCA CC-3' (SEQ ID NO: 34)

AHPLP-D (37 mer; Tm value: 58.6° C.; restriction enzyme SpeI site was added to the terminus.)
5'-ATA TAT ACT AGT GTT TTG TTG TGG TTA TTG GTA GTA C-3' (SEQ ID NO: 35)<

Primers to Amplify MRH1 Gene Promoter>

MRH1P-U (47 mer; Tm value: 71.1° C.; restriction enzyme NotI site was added to the terminus.)
5'-AGC TAG CTA GCG GCC GCG ATG GAA GAT GCA ACT TGC AAA TGT AGT CC-3' (SEQ ID NO: 36)

MRH1P-D (47 mer; Tm value: 64.1° C.; restriction enzyme SpeI site was added to the terminus.)
5'-AGC TAG CTA CTA GTG TTA TTT TTC TTC TTT GTT CTG TGG GTT AAA GG-3' (SEQ ID NO: 37)

<Primers to Amplify TDH3 Gene Promoter (Control)>

TDH3P-U (42 mer; Tm value: 69.5° C.; restriction enzyme NotI site was added to the terminus.)

5'-AGC TAG CTA GCG GCC GCG TTG AAT GTT AGC GTC AAC AAC AAG-3' (SEQ ID NO: 38)

TDH3P-D (47 mer; Tm value: 62.3° C.; restriction enzyme SpeI site was added to the terminus.)

5'-AGC TAG CTA CTA GTT TGT TTG TTT ATG TGT GTT TAT TCG AAA CTA AG-3' (SEQ ID NO: 39)<

Primers to Amplify PDC1 Gene Promoter (control)>

PDC1P-U (42 mer; Tm value: 67.1° C.; restriction enzyme NotI site was added to the terminus.)

5'-AGC TAG CTA GCG GCC GCG TTG AAT GTT AGC GTC AAC AAC AAG-3' (SEQ ID NO: 40)

PDC1P-D (37 mer; Tm value: 56.4° C.; restriction enzyme SpeI site was added to the terminus.)

5'-TAT ATA CTA GTT TGA TTG ATT TGA CTG TGT TAT TTT G-3' (SEQ ID NO: 41)

The PCR fragment obtained was subcloned into pBluescriptII SK+ vector (TOYOBO). A series of reaction procedures were performed according to the common DNA-subcloning method. More specifically, the above-mentioned vector digested with NotI and SpeI restriction enzymes (TAKARA BIO INC.) were ligated by T4 DNA ligase to each promoter fragment digested with the same restriction enzymes. The LigaFast Rapid DNA Ligation (Promega) was used for T4 DNA Ligase reaction; the details followed the attached protocol.

Subsequently, E. coli was transformed by adding ligation reaction mixture to E. coli competent cells. JM109 strain (TOYOBO) was used as E. coli competent cells; the handling details followed the attached protocol. Colonies were selected on an LB plate containing 100 μg/mL ampicillin, and plasmid DNA was prepared from each selected colonies, followed by confirmation by colony PCR using primer DNA set forth in SEQ ID NOs: 26-41, and then each promoter sequence was subcloned. The detailed manual of a series of procedures such as ethanol precipitation and restriction enzyme treatment followed the Molecular Cloning—A Laboratory Manual second edition—(Maniatis et al., Cold Spring Harbor Laboratory press. 1989).

Each vector containing the promoter sequence isolated was prepared by the alkaline extraction method, and was column-purified by the GFX DNA Purification kit (Amersham Pharmacia Biotech). Subsequently, DNA concentrations were measured by spectrophotometer, the Ultro spec 3000 (Amersham Pharmacia Biotech), and sequencing reaction was carried out using a DNA sequencing kit, the Big Dye Terminator Cycle Sequencing Ready Reaction Kit (PE Applied Biosystems). The reaction samples were applied to a sequence analysis instrument, the ABI PRISM 310 Genetic Analyzer (PE Applied Biosystems), to determine the sequences of the 6 promoters. The detailed usage of the instrument followed the attached manual of the instrument. The DNA sequences determined by the sequence analysis are given in SEQ ID NOs: 1-6.

Embodiment 3

Construction of Recombinant Vectors

Figure 2:
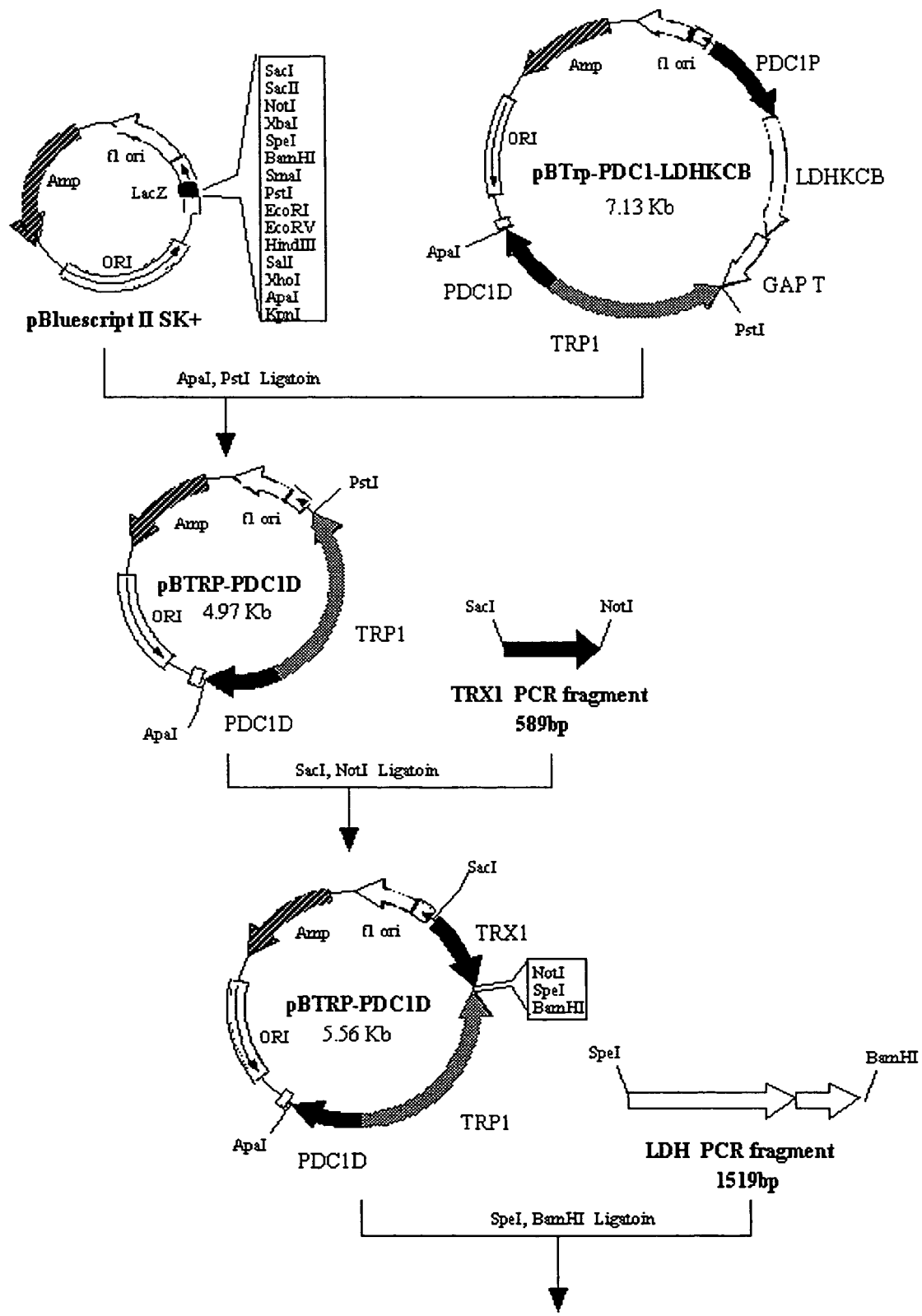
FIG. 2 is a diagram showing part of the construction process of a chromosome-integrating vector.
Figure 3:
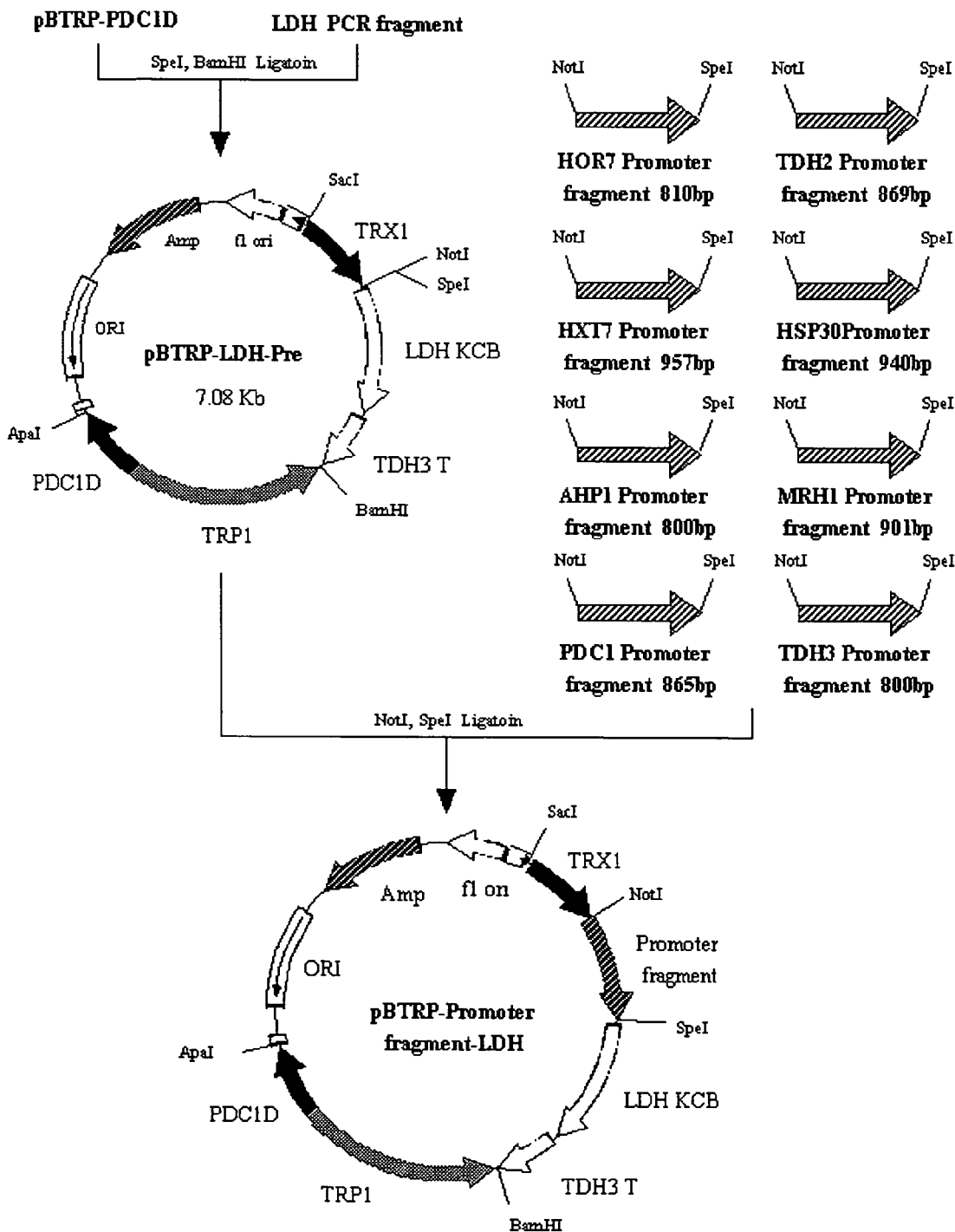
FIG. 3 is a diagram showing part of the construction process of a chromosome-integrating vector.
Figure 4:
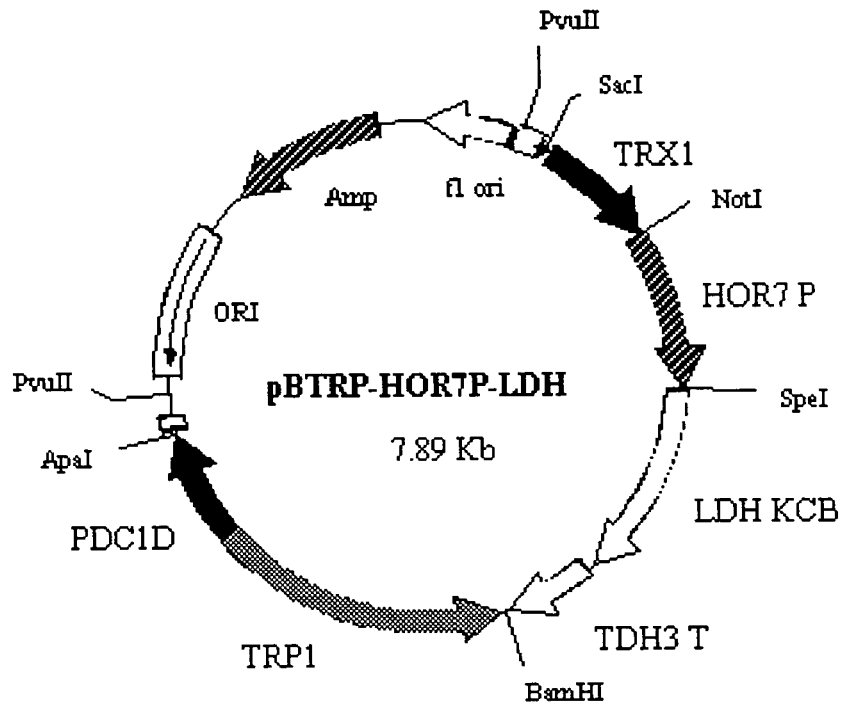
FIG. 4 is a diagram showing the map of the pBTRP—HOR7P-LDH vector.
Figure 5:
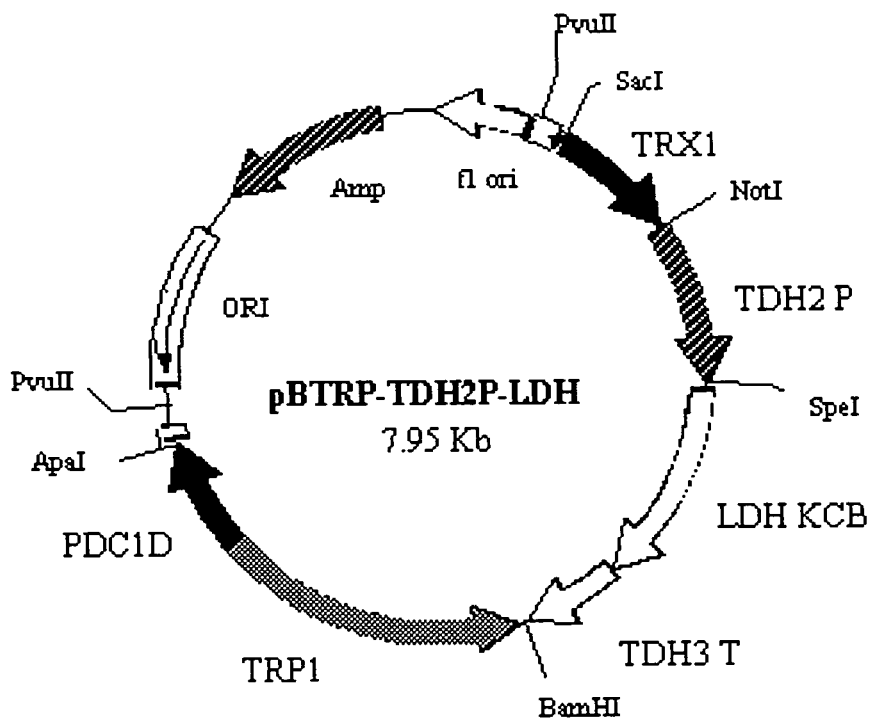
FIG. 5 is a diagram showing the map of the pBTRP-TDH2P-LDH vector.
Figure 6:
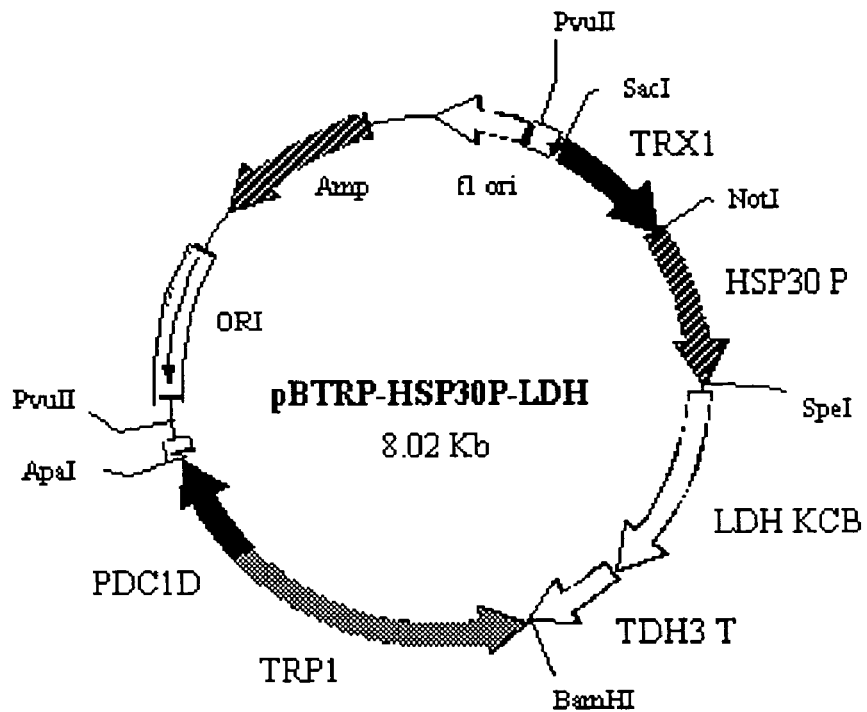
FIG. 6 is a diagram showing the map of the pBTRP-HSP30P-LDH vector.
Figure 7:
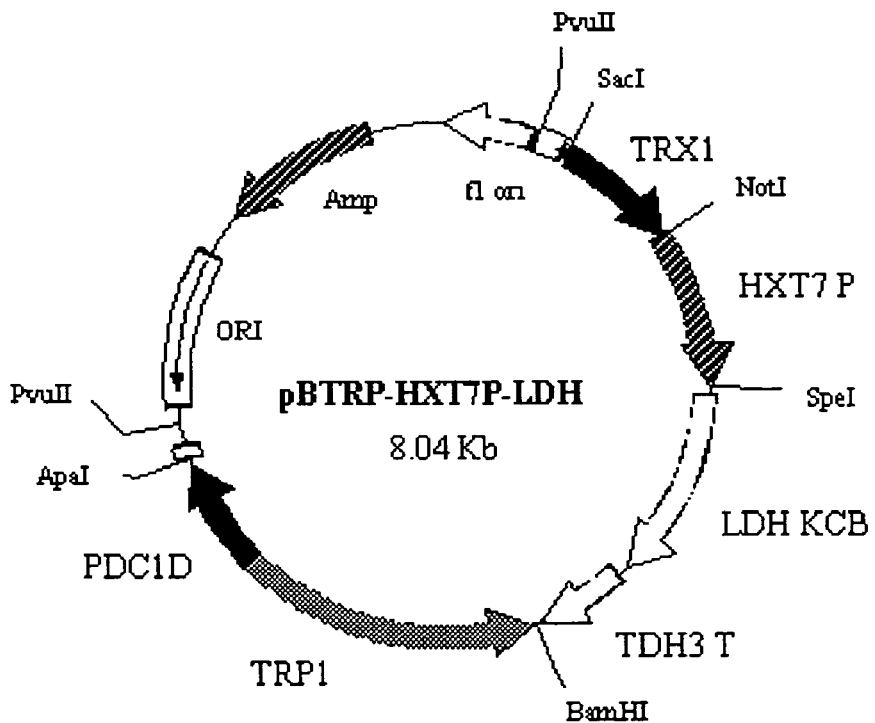
FIG. 7 is a diagram showing the map of the pBTRP-HXT7P-LDH vector.
Figure 8:
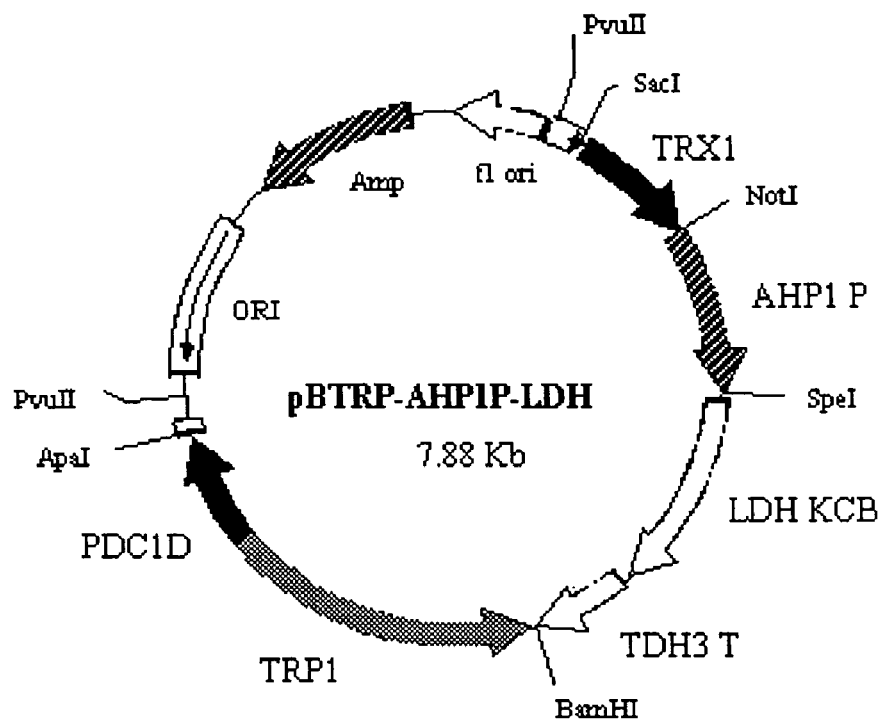
FIG. 8 is a diagram showing the map of the pBTRP-AHP1P-LDH vector.
Figure 9:
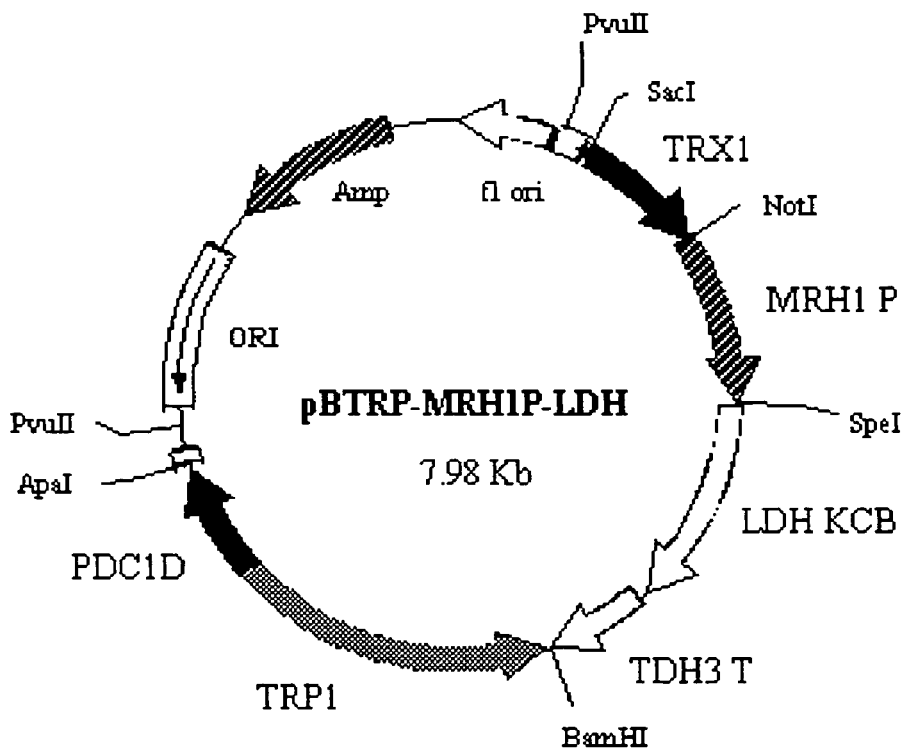
FIG. 9 is a diagram showing the map of the pBTRP-MRH1P-LDH vector.
Figure 10:
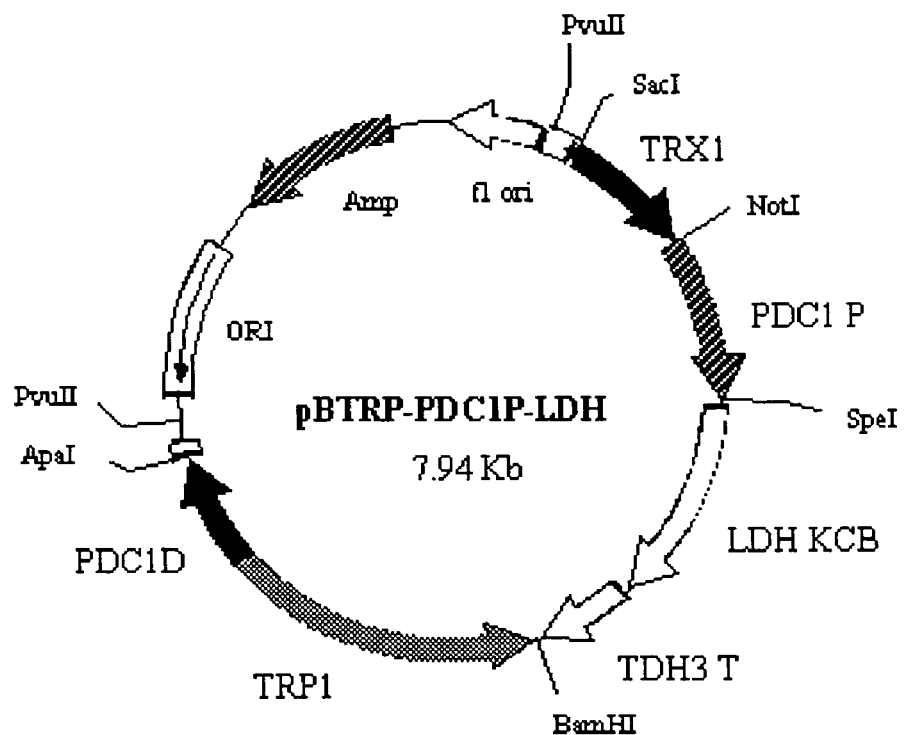
FIG. 10 is a diagram showing the map of the pBTRP-PDC1P-LDH vector.
Figure 11:
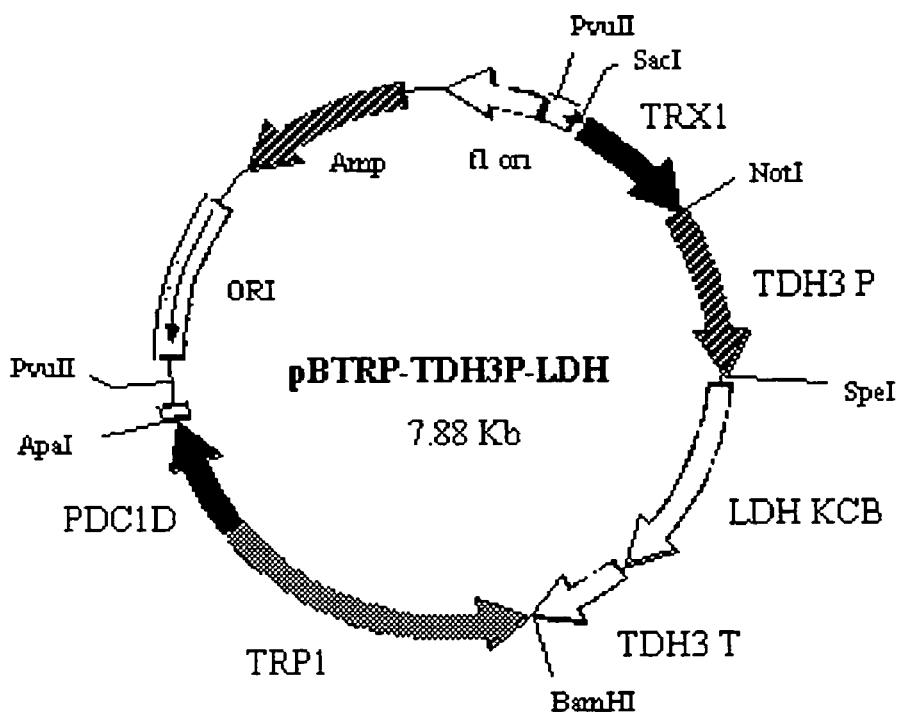
FIG. 11 is a diagram showing the map of the pBTRP-TDH3P-LDH vector.
Figure 12:
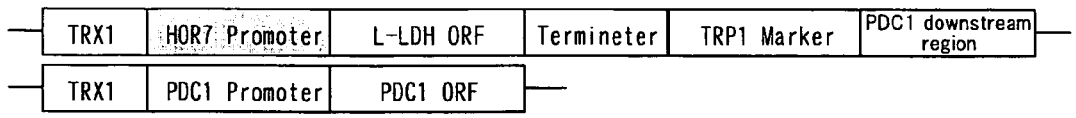
FIG. 12 is a diagram showing the chromosomal structure of the transformant strain carrying the pBTRP-HOR7P-LDH vector.
Figure 13:
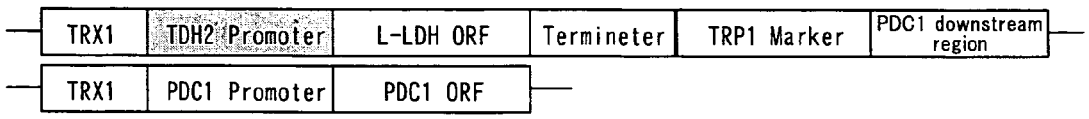
FIG. 13 is a diagram showing the chromosomal structure of the transformant strain carrying the pBTRP-TDH2P-LDH vector.
Figure 14:
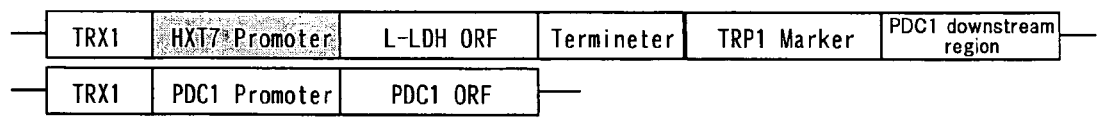
FIG. 14 is a diagram showing the chromosomal structure of the transformant strain carrying the pBTRP-HXT7P-LDH vector.
Figure 15:
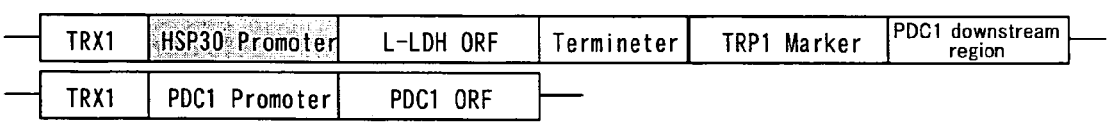
FIG. 15 is a diagram showing the chromosomal structure of the transformant strain carrying the pBTRP-HSP30P-LDH vector.
Figure 16:
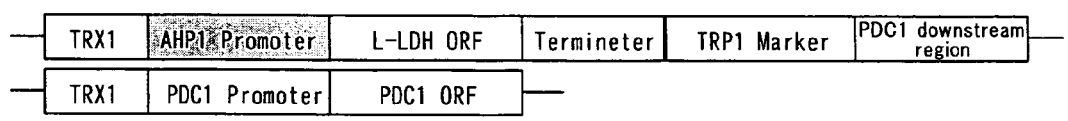
FIG. 16 is a diagram showing the chromosomal structure of the transformant strain carrying the pBTRP-AHP1P-LDH vector.
Figure 17:
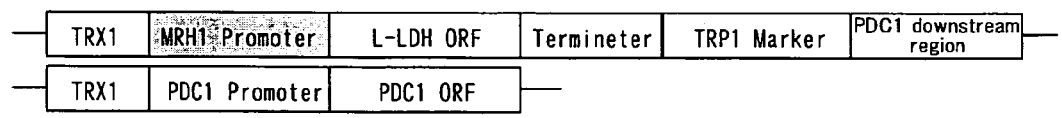
FIG. 17 is a diagram showing the chromosomal structure of the transformant strain carrying the pBTRP-MRH1P-LDH vector.
Figure 18:
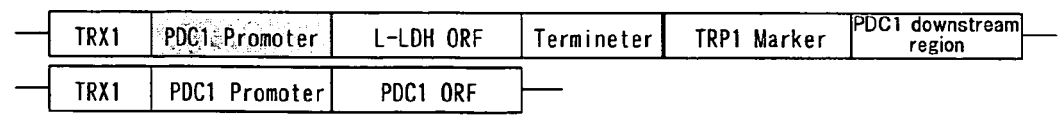
FIG. 18 is a diagram showing the chromosomal structure of the transformant strain carrying the pBTRP-PDC1P-LDH vector.
Figure 19:
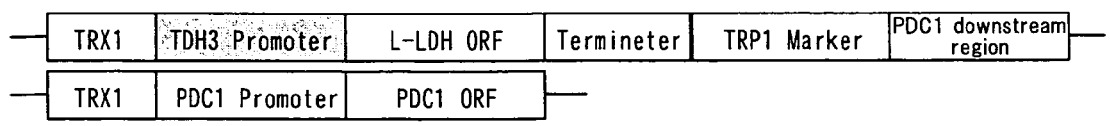
FIG. 19 is a diagram showing the chromosomal structure of the transformant strain by mapping the pBTRP-TDH3P-LDH vector.

The newly constructed chromosome-integrating vectors were each named pBTRP—HOR7P-LDH vector, pBTRP-TDH2P-LDH vector, pBTRP-HXT7P-LDH vector, pBTRP—HSP30P-LDH vector, pBTRP-AHP1P-LDH vector, and pBTRP-MRH1P-LDH vector. Also, vectors that can express L-LDH gene from TDH3 gene promoter and PDC1 gene promoter were constructed as the controls to compare the promoters, which were named pBTRP-TDH3P-LDH vector and pBTRP-PDC1P-LDH vector, respectively. Hereinafter, the construction processes of vectors in this embodiment are described in detail based on FIG. 2 and FIG. 3, however, the procedures of vector construction are not limited thereto. A series of reaction procedures in the vector construction followed the common DNA subcloning methods, using TAKARA BIO's enzymes.

(Construction of a Pre-Vector)

According to the common DNA subcloning method, PBTRP-LDH pre-vector was constructed. To construct the pBTRP-PDC1D vector, a fragment obtained by digesting the pBTrp-PDC1-LDHKCB vector, which the inventors have already constructed (described in Japanese Published Unexamined Patent Application No. 2003-259878), with ApaI and PstI restriction enzymes was inserted into pBluescriptII SK+ vector (TOYOBO) digested with the same restriction enzymes. Subsequently, the TRX1 fragment (700 bp) obtained by PCR amplification, followed by digestion with SacI and NotI restriction enzymes, and LDHKCB fragment (2,000 bp) obtained by PCR amplification, followed by digestion with SpeI and BamHI restriction enzymes were ligated to this vector one by one to construct the pBTRP-LDH pre-vector.

Here, the pBTrp-PDC1-LDHKCB vector was constructed in the following manner. That is, to effectively produce L-lactate dehydrogenase, a protein derived from a higher eukaryote (cattle), in yeast Saccharomyces cerevisiae, the DNA was synthesized using the procedures of Fujimoto et al. (Hideya Fujimoto; Production method of synthetic gene; Plant Cell Biology series 7; PCR experimental protocol; 1997; Shujunsha; p 95-100), known as a synthesis method of long-chain DNA, by designing novel gene sequences (SEQ ID NO: 42) of DNA that encodes amino acid sequence of bovine L-lactate dehydrogenase, which are not naturally-occurring, according to the following points for designing (the synthesized DNA was named LDHKCB sequence.). Yeast chromosome-integrating vector pBTRP-PDC1-LDHKCB was constructed using all the synthesized LDHKCB sequences (See upper right of FIG. 2). In addition, the LDHKCB sequence digested with EcoRI enzyme was ligated to pCR2.1TOPOVector (Invitrogen) that was similarly digested with EcoRI according to the common procedures, and the resulting vector was named pBTOPO-LDHKCB.

1. The PDC1P fragment for the construction of the pBTrp-PDC1-LDHKCB was isolated by PCR amplification using genomic DNA of Saccharomyces cerevisiae YPH strain (Stratagene) as a template. Genomic DNA of Saccharomyces cerevisiae YPH strain was prepared using a genome preparation kit, the Fast DNA Kit (Bio 101); the details followed the attached protocol. DNA concentrations were measured by spectrophotometer, the Ultro spec 3000 (Amersham Pharmacia Biotech). The Pyrobest DNA Polymerase (TAKARA) was used as an amplifying enzyme in PCR reaction, to have distinguished accuracy of amplified fragments.

Total 50 μL of reaction solution was prepared, which contained 50 ng/sample of genomic DNA of Saccharomyces cerevisiae YPH strain, prepared according to the above procedures, 50 pmol/sample of primer DNA, and 0.2 units/sample of the Pyrobest DNA Polymerase. For DNA amplification, the reaction solution was applied to a PCR amplifying instrument, the Gene Amp PCR system 9700 (PE Applied Biosystems). The reaction conditions of the PCR amplifying instrument were: heat treatment at 96° C. for 2 min, followed by 25 cycles (1 cycle of 3 temperatures: 96° C. for 30 min, 53° C. for 30 sec, and 72° C. for 60 sec), and finally incubation at 4° C. The amplified fragments of PDC1 primer were electrophoresed on 1% TBE agarose gel to confirm gene amplification. In this reaction, synthetic DNAs (Sawady technology) were used as primers, whose sequences are as follows:

PDC1P-LDH-U (31 mer; Tm value: 58.3° C.) Restriction enzyme BamHI site was added to the terminus: ATA TAT GGA TCC GCG TTT ATT TAC CTA TCT C (SEQ ID NO: 44)

PDC1P-LDH-D (31mer; Tm value: 54.4° C.) Restriction enzyme EcoRI site was added to the terminus: ATA TAT GAA TTC TTT GAT TGA TTT GAC TGT G (SEQ ID NO: 45)

2. Gene fragments, PDC1 gene promoter fragment (PDC1P: 971 bp) and the downstream region of the PDC1 gene fragment (PDC1D: 518 bp), were isolated by PCR amplification, as described above, using genomic DNA of Saccharomyces cerevisiae YPH strain as a template. The procedures of PCR amplification are as described above, however, the following primers were used for the amplification of the fragment of the downstream region of the PDC1 gene:

PDC1D-LDH-U (34 mer; Tm value: 55.3° C.) Restriction enzyme XhoI site was added to the terminus: ATA TAT CTC GAG GCC AGC TAA CTT CTT GGT CGA C (SEQ ID NO: 46)

PDC1D-LDH-D (31 mer; Tm value: 54.4° C.) Restriction enzyme ApaI site was added to the terminus: ATA TAT GAA TTC TTT GAT TGA TTT GAC TGT G (SEQ ID NO: 47)

3. The PDC1P and PDC1D gene amplified fragments obtained in the above reaction were each extracted by ethanol precipitation, and then PDC1P and PDC1D amplified fragments were digested with BamHI/EcoRI and XhoI/ApaI restriction enzymes, respectively. All the enzymes used below were products of TAKARA HOLDINGS INC. In addition, the detailed manual of a series of procedures for ethanol precipitation and restriction enzyme digestion followed the Molecular Cloning—A Laboratory Manual second edition—(Maniatis et al., Cold Spring Harbor Laboratory press. 1989). The PDC1P fragments, amplified by the above PCR method and digested with a restriction enzyme, were ligated by T4 DNA ligase to pBluescriptII SK+ vector (TOYOBO) treated with BamHI/EcoRI restricted enzyme (TAKARA) and dephosphorylating enzyme Alkaline Phosphatase (BAP, TAKARA). The LigaFast Rapid DNA Ligation System (Promega) was used for the T4 DNA ligase reaction; the details followed the attached protocol.

4. Competent cells were transformed using the solution of the ligation reaction. E. coli JM109 strain (TOYOBO) was used as competent cell; the details followed the attached protocol. The resulting culture medium was plated onto an LB plate containing 100 μg/mL antibiotic ampicillin, and was incubated overnight. Colonies grown were checked by colony PCR method using primer DNA for the insert fragment; in addition, plasmid DNA solution was prepared by mini-prep and digested by restriction enzymes for confirmation, and thereby isolated the pBPDC1P vector.

5. Next, the pBTOPO-LDHKCB vector constructed above was treated with EcoRI restriction enzyme and terminal-modifying enzyme, T4 DNA polymerase, and the resulting LDHKCB gene fragment was subcloned into a pBPDC1P vector treated with EcoRI restriction enzyme and terminal-modifying enzyme, T4 DNA polymerase, in the same manner as above, and thereby constructed the pBPDC1P-LDHKCB vector.

6. At the same time, the previously constructed pYLD1 vector was treated with EcoRI/AatII restriction enzymes and terminal modification enzyme, T4 DNA polymerase, and the resulting LDH gene (derived from Bifidobacterium longum) fragment was subcloned into the pBPDC1P vector treated with EcoRI restriction enzyme and terminal-modifying enzyme, T4 DNA polymerase, in the same manner as above, and thereby constructed pBPDC1P-LDH1 vector. The above-mentioned pYLD1 vector was introduced into E. coli (referred to as E. coli pYLD1), and was deposited to the International Patent Organism Depositary of the National Institute of Advanced Industrial Science and Technology (1-1-1 Tsukuba East, Tsukuba, Ibaraki) under the contract No. FERMBP-7423 according to the Budapest Treaty (original deposit day: Oct. 26, 1999).

7. Subsequently, this vector was treated with XhoI/ApaI and ligated to the PDC1D amplified fragment treated with restriction enzymes in the same manner, and thereby constructed the pBPDC1P-LDH vector. Finally, the pBPDC1P-LDHII vector treated with EcoRV was ligated to the Trp marker fragment obtained by treating pRS404 vector (Stratagene) with AatII/SspI and T4 DNA polymerase, and thereby constructed the pBTrp-PDC1-LDH vector.

8. Then, the pBPDC1P-LDHKCB vector was treated with ApaI/EcoRI restriction enzymes, on the other hand, a fragment containing the Trp marker was obtained by treating the pBTrp-PDC1-LDH vector with ApaI and StuI, and was ligated to the amplified fragment, and thereby constructed the chromosome-integrating pBTrp-PDC1-LDH-KCB vector, the final construct.

(Construction and Confirmation of the Final Vector)

The final vectors were each obtained by ligating the pre-vector PBTRP-LDH treated with NotI and SpeI to the promoter sequence obtained in the above embodiment 2, treated with the same enzymes. The detailed maps are given in FIG. 4 to FIG. 11 for the pBTRP—HOR7P-LDH vector, pBTRP-TDH2P-LDH vector, pBTRP-HXT7P-LDH vector, pBTRP—HSP30P-LDH vector, pBTRP-AHP1P-LDH vector, and pBTRP-MRH1P-LDH vector constructed in the invention, and pBTRP-TDH3P-LDH vector and pBTRP-PDC1P-LDH vector as the controls for comparison.

The LigaFast Rapid DNA Ligation (Promega) was used for the above DNA ligation reaction; the details followed the attached protocol. E. coli JM109 strain (TOYOBO) was used as competent cells for the transformation with ligation reaction solution. In all the cases, colonies were selected on an LB plate containing 100 □g/mL antibiotic ampicillin, and objective vectors were confirmed by colony PCR using each colony. The detailed manual of a series of procedures for ethanol precipitation and restriction enzyme digestion followed the Molecular Cloning—A Laboratory Manual second edition—(Maniatis et al., Cold Spring Harbor Laboratory press. 1989).

Embodiment 4

Preparation of Yeast Transformants

A yeast strain of host IFO2260 (a strain registered to the Institute of Fermentation), lacking tryptophan synthetic ability, was cultured at 30° C. in 10 mL of YPD medium to logarithmic growth phase (OD600 nm=0.8). Competent cells were prepared from them using the Frozen-EZ Yeast Transformation II kit (ZYMO RESEARCH). According to the attached protocol of the kit, these competent cells were transformed with the chromosome-integrating vectors constructed in the above embodiment 4, which were digested with PvuII restriction enzyme. Eight concrete vectors introduced included the pBTRP—HOR7P-LDH vector, pBTRP-TDH2P-LDH vector, pBTRP-HXT7P-LDH vector, pBTRP-HSP30P-LDH vector, pBTRP-AHP1P-LDH vector, and pBTRP-MRH1P-LDH vector constructed in the invention, and pBTRP-TDH3P-LDH vector and pBTRP-PDC1P-LDH vector constructed as the controls for comparison. These transformant samples were washed, and were dissolved in 100 µL of sterile water and plated onto tryptophan-selection medium, and then each transformant was selected at 30° C. in static culture.

Each colony obtained was isolated again on a new tryptophan-selection medium, and those maintaining stable growth capacity were determined as candidate transformants. Subsequently, these candidate strains were cultured overnight in 2 mL of YPD medium, and genomic DNA was prepared from them using a genomic DNA preparation kit, the GenToRukun™ for yeasts (TAKARA BIO INC.). PCR analysis was performed using each prepared genomic DNA as a template, and those for which the presence of introduced genes was confirmed were determined as transformants. The gene structures on the chromosome within each yeast transformant are given in FIG. 12 to FIG. 19.

Embodiment 5

Investigation of Each Promoter by Fermentation Test

The amounts of L-lactic acid produced within the prepared transformants were measured, and the activities (in the presence of an organic acid) of the 6 promoters obtained were investigated in comparison with the amounts of lactic acid produced using the TDH3 gene promoter and PDC1 gene promoter, known as high-level expression promoters. Eight transformants obtained were inoculated into 5 mL of YPD liquid medium and cultured at 30° C. overnight with shaking at 130 rpm, and an original issue stock (OD600 nm=1.2) was obtained. After inoculating 2 mL culture each into 20 mL of YPD medium containing 10% glucose and 20 mL of cane juice medium containing approximately 10% sucrose (total volume: 22 mL) and adding 1 g of calcium carbonate (Nacalai tesque) as a neutralizing agent, static culture was performed at 30° C. for 4 days. To measure the amounts of lactic acid produced, the multifunctional biosensor BF-4 instrument (Oji Scientific Instruments) was used; the details of the specification followed the attached manual. The results are given in FIG. 20 and FIG. 21.

Figure 20:
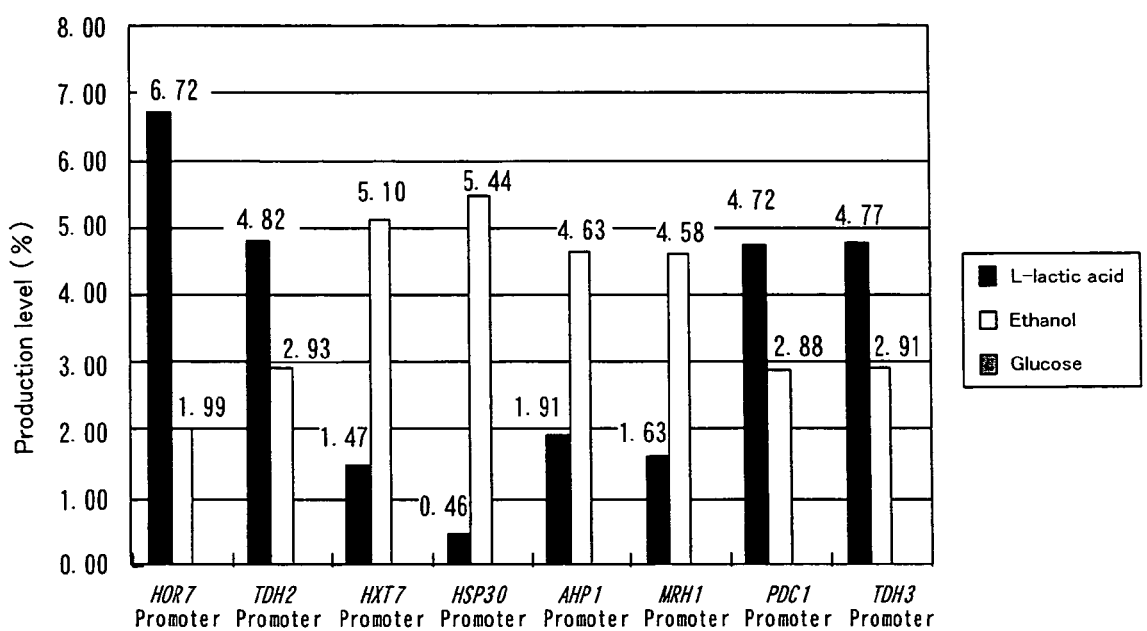
FIG. 20 is a graph showing the results of a lactic acid fermentation test in various transformant strains of yeast (YPD medium)
Figure 21:
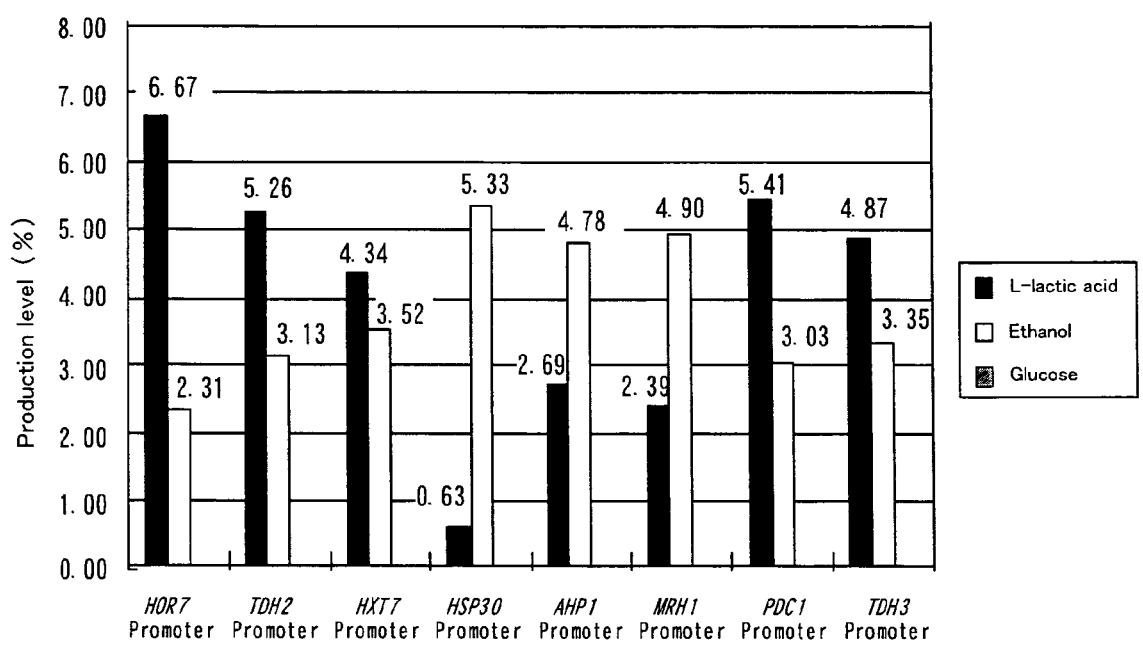
FIG. 21 is a graph showing the results of the lactic acid fermentation test in various transformant strains of yeast (cane juice medium).

As shown in FIG. 20 and FIG. 21, the HOR7 gene promoter, TDH2 gene promoter, and HXT7 gene promoter showed comparable or higher expression levels compared with the PDC1 control promoter and TDH3 control promoter. On the other hand, the HSP30 gene promoter, AHP1 gene promoter, MRH1 gene promoter did not show higher expression levels than the control, however, the expression of these promoters was considered to be in a lower activated state due to small amounts of lactic acid produced; thus, addition of organic acids such as lactic acid to the culture system from outside or induction of the lactic acid expression from a constitutive promoter are expected to provide higher expression levels.

Sequence table: Free text

SEQ ID NOs: 10-41: Synthetic primer

SEQ ID NOs: 42 and 43: Synthetic DNA

SEQ ID NOs: 44-47: Synthetic primer

The invention claimed is:

1. A DNA construct comprising:
   a promoter DNA comprising SEQ ID NO: 1 or a fragment thereof that acts as a promoter for the high osmolarity response 7 (HOR7) gene in *Saccharomyces cerevisiae*; and
   a DNA that is operatively associated with the promoter DNA and encodes a protein having lactate dehydrogenase activity.

2. The DNA construct according to claim 1, further comprising DNA that can homologously recombine with a yeast pyruvate decarboxylase 1 (PDC1) gene.

3. A plasmid or virus comprising the DNA construct of claim 1.

4. A cell that has been transformed with the DNA construct of claim 1.

5. The transformed cell of claim 4, wherein said DNA construct has been integrated into a chromosome.

6. The transformed cell of claim 4 that is a yeast.

7. The transformed yeast cell of claim 6,
   wherein said DNA construct has been integrated into a pyruvate decarboxylase (PDC1) gene of said yeast cell.

8. A method for producing lactic acid comprising:
culturing the cell of claim 4, and
recovering lactic acid.

9. A method for producing lactic acid comprising:
culturing the cell of claim 7, and
recovering lactic acid.

10. A DNA construct comprising:
a promoter DNA comprising SEQ ID NO: 1; and
a DNA that is operatively associated with the promoter DNA and encodes a protein having lactate dehydrogenase activity.

\* \* \* \* \*

UNITED STATES PATENT AND TRADEMARK OFFICE
CERTIFICATE OF CORRECTION

PATENT NO. : 7,696,333 B1  Page 1 of 1
APPLICATION NO. : 10/578614
DATED : April 13, 2010
INVENTOR(S) : Nobuhiro Ishida et al.

It is certified that error appears in the above-identified patent and that said Letters Patent is hereby corrected as shown below:

(73), Assignee, "Kabuhsiki Kaisha Toyota Chuo" should read --Kabushiki Kaisha Toyota Chuo Kenkyusho--

(73), Assignee, "Toyota Jidosha Kabuhsiki Kaisha" should read --Toyota Jidosha Kabushiki Kaisha--

Abstract, "associated gene gene" should read --associated gene (MRH1 gene)--

Signed and Sealed this

Sixth Day of July, 2010

David J. Kappos
*Director of the United States Patent and Trademark Office*

SEQUENCE LISTING

```
<160> NUMBER OF SEQ ID NOS: 47

<210> SEQ ID NO 1
<211> LENGTH: 810
<212> TYPE: DNA
<213> ORGANISM: Saccharomyces cerevisiae

<400> SEQUENCE: 1
ctcgctcgca gccacgggtc aacccgattg ggatcacccc actggggccc aagcctgata        60
tccgacctcc atgaaatttt ttttttttctt tcgattagca cgcacacaca tcacatagac       120
tgcgtcataa aaatacacta cggaaaaacc ataaagagca aagcgatacc tacttggaag       180
gaaaaggagc acgcttgtaa gggggatggg ggctaagaag tcattcactt tcttttccct       240
tcgcggtccg gacccgggac ccctcctctc cccgcacgat ttcttcctttt catatcttcc      300 ttttattcct atcccgttga agcaaccgca ctatgactaa atggtgctgg acatctccat       360
ggctgtgact tgtgtgtatc tcacagtggt aacggcaccg tggctcggaa acggttcctt       420
cgtgacaatt ctagaacagg ggctacagtc tcgataatag aataataagc gcatttttgc       480
tagcgccgcc gcggcgcccg tttcccaata gggaggcgca gtttatcggc ggagctctac       540
ttcttcctat ttgggtaagc ccctttctgt tttcggccag tggttgctgc aggctgcgcc       600
ggagaacata gtgataaggg atgtaacttt cgatgagaga attagcaagc ggaaaaaaac       660
tatggctagc tgggagttgt ttttcaatca tataaaaggg agaaattgtt gctcactatg       720
```

```
tgacagtttc tgggacgtct taacttttat tgcagaggac tatcaaatca tacagatatt      780
gtcaaaaaaa aaaaagacta ataataaaaa                                       810

<210> SEQ ID NO 2
<211> LENGTH: 869
<212> TYPE: DNA
<213> ORGANISM: Saccharomyces cerevisiae

<400> SEQUENCE: 2
cttgacgggt attctgagca tcttactcag tttcaagatc ttttaatgtc caaaaacatt       60
tgagccgatc taaatacttc tgtgttttca ttaatttata aattgtactc ttttaagaca      120
tggaaagtac caacatcggt tgaaacagtt tttcatttac atatggttta ttggttttc       180 cagtgaatga ttatttgtcg ttacccttc gtaaagttc taacacgttt ttaagtattg       240
tttagttgct ctttcgacat atatgattat ccctgcgcgg ctaaagttaa agatgcaaaa      300
aacgtaagac aactgaagtt aatttacgtc aattaagttt tccagggtaa tgatgttttg      360
ggcttccact aattcaataa gtgtgtcatg aaatacgttg tgaagagcat ccagaaataa      420
tgaaaagaaa caacgaaact gggtcggcct gttgtttctt ttctttacca cgtgatctgc      480
ggcatttaca ggaagtcgct cgttttgcgc agttgttgca acgcagctac ggctaacaaa      540
gcctagtgga actcgactga tgtgttaggg cctaaaactg tggtgacag ctgaagtgaa       600 ctattcaatc caatcatgtc atggctgtca caaagacctt gcggaccgca cgtacgaaca      660
catacgtatg ctaatatgtg ttttgatagt acccagtgat cgcagacctg caatttttt       720 gtaggtttgg aagaatatat aaaggttgca ctcattcaag atagttttt tcttgtgtgt      780 ctattcattt tattattgtt tgtttaaatg ttaaaaaaac caagaactta gtttcaaatt      840
aaattcatca cacaaacaaa caaaacaaa                                        869

<210> SEQ ID NO 3
<211> LENGTH: 957
<212> TYPE: DNA
<213> ORGANISM: Saccharomyces cerevisiae

<400> SEQUENCE: 3
gccctgctaa acacgcccta ctaaacactt caaaagcaac ttaaaatatt tttatctaat       60
tatagctaaa acccaatgtg aaagacatat catactgtaa aagtgaaaaa gcagcaccgt      120
tgaacgccgc aagagtgctc ccataacgct ttactagagg ctagatttt aatggcccct       180 tcatggagaa gttatgagga caaatcccac tacagaaagc gcaacaaatt tttttttccg      240
taacaacaaa catctcatct agtttctgcc ttaaacaaag ccgcagccag agccgttttt      300
ccgccatatt tatccaggat tgttccatac ggctccgtca gaggctgcta cgggatgttt      360 ttttttacc ccgtggaaat gaggggtatg caggaatttg tgcggggtag gaaatctttt      420 tttttttag gaggaacaac tggtggaaga atgcccacac ttctcagaaa tgcatgcagt      480
ggcagcacgc taattcgaaa aaattctcca gaaaggcaac gcaaaatttt ttttccaggg      540
aataaacttt ttatgaccca ctacttctcg taggaacaat ttcgggcccc tgcgtgttct      600
tctgaggttc atcttttaca tttgcttctg ctggataatt tcagaggca acaaggaaaa       660 attagatggc aaaagtcgt ctttcaagga aaatcccca ccatctttcg agatcccctg        720
taacttattg gcaactgaaa gaatgaaaag gaggaaaata caaatatac tagaactgaa       780 aaaaaaaag tataaataga gacgatatat gccaatactt cacaatgttc gaatctattc      840
ttcatttgca gctattgtaa aataataaaa catcaagaac aaacaagctc aacttgtctt      900
```

```
ttctaagaac aaagaataaa cacaaaaaca aaaagttttt ttaattttaa tcaaaaa          957
```

```
<210> SEQ ID NO 4
<211> LENGTH: 940
<212> TYPE: DNA
<213> ORGANISM: Saccharomyces cerevisiae

<400> SEQUENCE: 4
cgctgaatac gtcctgtcaa ttcaaatata tcacgttgtg agcagcccta aagaagaaaa       60
cctcaacagc agtattacta ttacaatcaa acaactttag tgccgcgtga taccgggggt      120
tgaagtgggt gcattgagcc gtattcttct tccccgtaag aaagttgtgt atccttttta      180
ctgcgttgta atagcttctg aaacctaaa aaatgaacgc tatgtagctc atatccgttt       240
tgcataagta agaataacta cttgtgcagg gtgccgaaag ggatggaaaa ccgctgcagc      300
aacccttgtt acatacagtc ggatccatct gacttacttt ccttgcgtct ccctgcgcga      360
ttttgttggc cattttccag atcctctaga attttcaag ggtcgagccg taggaggatt       420
ctctcagaag gcaaaaacgc atcgaaagcg tgctttgtaa gaatatttgg tatggctaaa      480
gtaagcaaag ccatatcccg atcccgatcc cgactcttat tccgatccct tccgccacat      540
cctgcatgtt tattcgaata ccaaattagc tcatcttcgt tatttcatca tccctttctg      600
ctatggcaag gacaagtttt tttctagcat ctcatcgaaa actttcctct ccctaattgg      660
ccaaagtttt catattcatc atcagttaga aagtataata tcaatccctt acctcattac      720
aagttgtatc acactaaaaa aatcatatat aagtctgtga gagtcttcaa ttatttagcg      780
taacacctat tcactttcta atcttgtttc ttgttttac attctgcaat acaacacaac       840
aacaaatatt aactcaatta ttattattta taattacaaa aacaaaacaa caagtttgag      900
actttaatat cttttgatta ctaaaaacaa caaatttcaa                            940
```

```
<210> SEQ ID NO 5
<211> LENGTH: 800
<212> TYPE: DNA
<213> ORGANISM: Saccharomyces cerevisiae

<400> SEQUENCE: 5
cgcatccgaa ttcaatgtag cacctgagat ctcaaatagc ttttggccaa tcctaatctt       60
gaaaacttca tggtttggta aaagctcggg ggtagtttct aactcttttg tataaaccac      120
gatctcgccc ttttggccag acatctgata tgagcgtgcg tgtgagtgac tttacacttg      180
tctatccacg tcctgaagtt gttcgtgttc tttggatatt cgtgttcaag ctaataatga      240
gcctttaagg taatacaatt tataaaccac caccttggcc tcgatctatt gcgcttatgt      300
tgtctattag taatcaagaa aagaacccta aatcatcggc gtcccctgtg gggctctcgg      360
aaaaaccggt cctgacgtca ctgaaaagat ttcggcacat ggtcatggga ccagagaaaa      420
attaatccga catgtggaat atttccttcc gttaaggtag tgagcgcgga ttttttctga      480
tttgtaatta tacggggagc tctggccaaa aaggtcagta tttggtgatg aagttgaata      540
tcatcttttg atttttcttct gtatcattct ttttctttt ccacacccct tccggacggt       600
attcacatat tgttgagagg ttaaatgaaa aataaagggg tggaaaatta aggacgagat      660
gtaagggaaa agcataaacg aaacattata taaggagca caatttcctc tcccttgcca      720
attgtgcata taccgtttct ttataacgaa atttcaacaa accagaacaa cacaagtact      780
accaataacc acaacaaaac                                                  800
```

<210> SEQ ID NO 6
<211> LENGTH: 901
<212> TYPE: DNA
<213> ORGANISM: Saccharomyces cerevisiae

<400> SEQUENCE: 6

```
tcgatggaag atgcaacttg caaatgtagt ccggttacca agagacccaa acctcttcca      60
ctttactatt tctcctttga gaaatatatc agtttgcggt aataggtaat atgaaaaagg     120
caataaaaaa aagagatact tgtcaccatc tcgtctccct ttaccttttt tacttaatct     180
tcttcgtcgt catctgttcc atcccttttcc tagcttagtc ttctccggct agttcttagt    240
gcggtaagca aaaaaatagc gttttttttc cctcaccagg acttttttg ttaaccgaaa      300
atcggcatct ctagttttcc tggacaaaaa agacaaatg gaaataaaca ctcatacgaa      360
tcagtaaaga tgtaaataat cgcagtaacg actgcacaag gatgtcagaa aaagcagttt     420
aattccagaa gtggttttcc aatttatcac acatgtacat gaagggaaat gtttaaatac     480
ggtcttcgta aaacaaagga tctcttcacc tggtttcttc atttataagt agtgtctttt     540
tcggtaactt aagatatatc cttatttctt tcccacttct cgttatttct tcttttttccc    600
ttttcaagtt cttcttttta tttattatta agcttatttt aattcttaga tcgttgtcac     660
tatcttttgt ccttattgtt aagaaacatt gcgaagaaaa agaataataa aagaaactca     720
gaaaaaaaag aagtttcctc gaacaaaaat attattattt caataacttt tctttctct     780
acatccaatt ttttgacccct attttaacat taattttttg ctttaatttt aactaatacc    840
taatttcact taatatctaa tcatcttcct ttaacccaca gaacaaagaa gaaaaataac    900
a                                                                    901
```

<210> SEQ ID NO 7
<211> LENGTH: 999
<212> TYPE: DNA
<213> ORGANISM: Bos taurus
<220> FEATURE:
<221> NAME/KEY: CDS
<222> LOCATION: (1)..(999)
<223> OTHER INFORMATION: Lactate Dehydrogenase

<400> SEQUENCE: 7

```
atg gca act ctc aag gat cag ctg att cag aat ctt ctt aag gaa gaa       48
Met Ala Thr Leu Lys Asp Gln Leu Ile Gln Asn Leu Leu Lys Glu Glu
 1               5                  10                  15 cat gtc ccc cag aat aag att aca att gtt ggg gtt ggt gct gtt ggc       96
His Val Pro Gln Asn Lys Ile Thr Ile Val Gly Val Gly Ala Val Gly
                20                  25                  30 atg gcc tgt gcc atc agt atc tta atg aag gac ttg gca gat gaa gtt      144
Met Ala Cys Ala Ile Ser Ile Leu Met Lys Asp Leu Ala Asp Glu Val
            35                  40                  45 gct ctt gtt gat gtc atg gaa gat aaa ctg aag gga gag atg atg gat      192
Ala Leu Val Asp Val Met Glu Asp Lys Leu Lys Gly Glu Met Met Asp
        50                  55                  60 ctc caa cat ggc agc ctt ttc ctt aga aca cca aaa att gtc tct ggc      240
Leu Gln His Gly Ser Leu Phe Leu Arg Thr Pro Lys Ile Val Ser Gly
    65                  70                  75                  80 aaa gac tat aat gtg aca gca aac tcc agg ctg gtt att atc aca gct      288
Lys Asp Tyr Asn Val Thr Ala Asn Ser Arg Leu Val Ile Ile Thr Ala
                85                  90                  95 ggg gca cgt cag caa gag gga gag agc cgt ctg aat ttg gtc cag cgt      336
Gly Ala Arg Gln Gln Glu Gly Glu Ser Arg Leu Asn Leu Val Gln Arg
               100                 105                 110
```

-continued

```
aac gtg aac atc ttt aaa ttc atc att cct aat att gta aaa tac agc    384
Asn Val Asn Ile Phe Lys Phe Ile Ile Pro Asn Ile Val Lys Tyr Ser
        115                 120                 125 cca aat tgc aag ttg ctt gtt gtt tcc aat cca gtc gat att ttg acc    432
Pro Asn Cys Lys Leu Leu Val Val Ser Asn Pro Val Asp Ile Leu Thr
130                 135                 140 tat gtg gct tgg aag ata agt ggc ttt ccc aaa aac cgt gtt att gga    480
Tyr Val Ala Trp Lys Ile Ser Gly Phe Pro Lys Asn Arg Val Ile Gly
145                 150                 155                 160 agt ggt tgc aat ctg gat tca gct cgc ttc cgt tat ctc atg ggg gag    528
Ser Gly Cys Asn Leu Asp Ser Ala Arg Phe Arg Tyr Leu Met Gly Glu
                165                 170                 175 agg ctg gga gtt cac cca tta agc tgc cat ggg tgg atc ctt ggg gag    576
Arg Leu Gly Val His Pro Leu Ser Cys His Gly Trp Ile Leu Gly Glu
            180                 185                 190 cat ggt gac tct agt gtg cct gta tgg agt gga gtg aat gtt gct ggt    624
His Gly Asp Ser Ser Val Pro Val Trp Ser Gly Val Asn Val Ala Gly
        195                 200                 205 gtc tcc ctg aag aat tta cac cct gaa tta ggc act gat gca gat aag    672
Val Ser Leu Lys Asn Leu His Pro Glu Leu Gly Thr Asp Ala Asp Lys
    210                 215                 220 gaa cag tgg aaa gcg gtt cac aaa caa gtg gtt gac agt gct tat gag    720
Glu Gln Trp Lys Ala Val His Lys Gln Val Val Asp Ser Ala Tyr Glu
225                 230                 235                 240 gtg atc aaa ctg aaa ggc tac aca tcc tgg gcc att gga ctg tca gtg    768
Val Ile Lys Leu Lys Gly Tyr Thr Ser Trp Ala Ile Gly Leu Ser Val
                245                 250                 255 gcc gat ttg gca gaa agt ata atg aag aat ctt agg cgg gtg cat ccg    816
Ala Asp Leu Ala Glu Ser Ile Met Lys Asn Leu Arg Arg Val His Pro
            260                 265                 270 att tcc acc atg att aag ggt ctc tat gga ata aaa gag gat gtc ttc    864
Ile Ser Thr Met Ile Lys Gly Leu Tyr Gly Ile Lys Glu Asp Val Phe
        275                 280                 285 ctt agt gtt cct tgc atc ttg gga cag aat gga atc tca gac gtt gtg    912
Leu Ser Val Pro Cys Ile Leu Gly Gln Asn Gly Ile Ser Asp Val Val
    290                 295                 300 aaa gtg act ctg act cat gaa gaa gag gcc tgt ttg aag aag agt gca    960
Lys Val Thr Leu Thr His Glu Glu Glu Ala Cys Leu Lys Lys Ser Ala
305                 310                 315                 320 gat aca ctt tgg ggg atc cag aaa gaa ctg cag ttt taa                999
Asp Thr Leu Trp Gly Ile Gln Lys Glu Leu Gln Phe
                325                 330
```

<210> SEQ ID NO 8
<211> LENGTH: 332
<212> TYPE: PRT
<213> ORGANISM: Bos taurus

<400> SEQUENCE: 8

```
Met Ala Thr Leu Lys Asp Gln Leu Ile Gln Asn Leu Leu Lys Glu Glu
1               5                  10                  15

His Val Pro Gln Asn Lys Ile Thr Ile Val Gly Val Gly Ala Val Gly
                20                  25                  30

Met Ala Cys Ala Ile Ser Ile Leu Met Lys Asp Leu Ala Asp Glu Val
            35                  40                  45

Ala Leu Val Asp Val Met Glu Asp Lys Leu Lys Gly Glu Met Met Asp
        50                  55                  60

Leu Gln His Gly Ser Leu Phe Leu Arg Thr Pro Lys Ile Val Ser Gly
65                  70                  75                  80
```

```
Lys Asp Tyr Asn Val Thr Ala Asn Ser Arg Leu Val Ile Ile Thr Ala
                 85                  90                  95
Gly Ala Arg Gln Gln Glu Gly Glu Ser Arg Leu Asn Leu Val Gln Arg
            100                 105                 110
Asn Val Asn Ile Phe Lys Phe Ile Ile Pro Asn Ile Val Lys Tyr Ser
        115                 120                 125
Pro Asn Cys Lys Leu Leu Val Val Ser Asn Pro Val Asp Ile Leu Thr
    130                 135                 140
Tyr Val Ala Trp Lys Ile Ser Gly Phe Pro Lys Asn Arg Val Ile Gly
145                 150                 155                 160
Ser Gly Cys Asn Leu Asp Ser Ala Arg Phe Arg Tyr Leu Met Gly Glu
                165                 170                 175
Arg Leu Gly Val His Pro Leu Ser Cys His Gly Trp Ile Leu Gly Glu
            180                 185                 190
His Gly Asp Ser Ser Val Pro Val Trp Ser Gly Val Asn Val Ala Gly
        195                 200                 205
Val Ser Leu Lys Asn Leu His Pro Glu Leu Gly Thr Asp Ala Asp Lys
    210                 215                 220
Glu Gln Trp Lys Ala Val His Lys Gln Val Val Asp Ser Ala Tyr Glu
225                 230                 235                 240
Val Ile Lys Leu Lys Gly Tyr Thr Ser Trp Ala Ile Gly Leu Ser Val
                245                 250                 255
Ala Asp Leu Ala Glu Ser Ile Met Lys Asn Leu Arg Arg Val His Pro
            260                 265                 270
Ile Ser Thr Met Ile Lys Gly Leu Tyr Gly Ile Lys Glu Asp Val Phe
        275                 280                 285
Leu Ser Val Pro Cys Ile Leu Gly Gln Asn Gly Ile Ser Asp Val Val
    290                 295                 300
Lys Val Thr Leu Thr His Glu Glu Ala Cys Leu Lys Lys Ser Ala
305                 310                 315                 320
Asp Thr Leu Trp Gly Ile Gln Lys Glu Leu Gln Phe
                325                 330

<210> SEQ ID NO 9
<211> LENGTH: 971
<212> TYPE: DNA
<213> ORGANISM: Saccharomyces cerevisiae

<400> SEQUENCE: 9
aagggtagcc tccccataac ataaactcaa taaatatat  agtcttcaac ttgaaaaagg      60
aacaagctca tgcaaagagg tggtacccgc acgccgaaat gcatgcaagt aacctattca    120
aagtaatatc tcatacatgt tcatgagggt aacaacatg  cgactgggtg agcatatgct    180
ccgctgatgt gatgtgcaag ataaacaagc aagacggaaa ctaacttctt cttcatgtaa    240
taaacacacc ccgcgtttat ttacctatct ttaaacttca acaccttata tcataactaa    300
tatttcttga gataagcaca ctgcacccat accttcctta aaagcgtagc ttccagtttt    360
tggtggttcc ggcttccttc ccgattccgc ccgctaaacg catattttg  ttgcctggtg    420 gcatttgcaa aatgcataac ctatgcattt aaaagattat gtatgctctt ctgactttc     480 gtgtgatgaa gctcgtggaa aaaatgaata atttatgaat ttgagaacaa ttctgtgttg    540
ttacggtatt ttactatgga ataattaatc aattggaggt tttatgcaaa tatcgtttga    600
atatttttcc gaccctttga gtactttct  tcataattgc ataatattgt ccgctgcccg    660
```

-continued

```
tttttctgtt agacggtgtc ttgatctact tgctatcgtt caacaccacc ttattttcta    720
actatttttt ttttagctca tttgaatcag cttatggtga tggcacattt ttgcataaac    780
ctagctgtcc tcgttgaaca taggaaaaaa aaatatatta acaaggctct ttcactctcc    840
ttgcaatcag atttgggttt gttcccttta ttttcatatt tcttgtcata ttcctttctc    900
aattattatt ttctactcat aaccacacgc aaaataacac agtcaaatca atcaaagatc    960
ccccaattct c                                                         971

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
cgtcgccttc actggtttag                                                 20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
caaaaaggcc aaagcaccag                                                 20

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
caaggtaagt tgaccggtat g                                               21

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
gatggaagag ttagagtcac cc                                              22

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tcatgggctg tttggtcttc                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 15
agcgtcgtag ttggcacctc                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
aattgcagtc agccgtgatg                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
tcgacagctt gctctgcttc                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
aaccaagcgt gggctaagag                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
ggtttccttg gcagcgtaag                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
gctgcctgtg ttcactccac                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
tggctgcaaa acgttaccac                                              20

<210> SEQ ID NO 22
```

```
<211> LENGTH: 22
<212> TYPE: DNA
<213> ORGANISM: Artificial Sequence
<220> FEATURE:
<223> OTHER INFORMATION: Synthetic primer

<400> SEQUENCE: 22
caacgaattg aacgctgctt ac                                              22

<210> SEQ ID NO 23
<211> LENGTH: 24
<212> TYPE: DNA
<213> ORGANISM: Artificial Sequence
<220> FEATURE:
<223> OTHER INFORMATION: Synthetic primer

<400> SEQUENCE: 23
attcaacggc ttccttaact tctg                                            24

<210> SEQ ID NO 24
<211> LENGTH: 23
<212> TYPE: DNA
<213> ORGANISM: Artificial Sequence
<220> FEATURE:
<223> OTHER INFORMATION: Synthetic primer

<400> SEQUENCE: 24
gttttcaagg aattagacac tgc                                             23

<210> SEQ ID NO 25
<211> LENGTH: 23
<212> TYPE: DNA
<213> ORGANISM: Artificial Sequence
<220> FEATURE:
<223> OTHER INFORMATION: Synthetic primer

<400> SEQUENCE: 25
caacagtctt ttgagtagca gtc                                             23

<210> SEQ ID NO 26
<211> LENGTH: 35
<212> TYPE: DNA
<213> ORGANISM: Artificial Sequence
<220> FEATURE:
<223> OTHER INFORMATION: Synthetic primer

<400> SEQUENCE: 26
atatatgcgg ccgctcgcag ccacgggtca acccg                                35

<210> SEQ ID NO 27
<211> LENGTH: 41
<212> TYPE: DNA
<213> ORGANISM: Artificial Sequence
<220> FEATURE:
<223> OTHER INFORMATION: Synthetic primer

<400> SEQUENCE: 27
atatatacta gttttattta ttagtctttt tttttttga c                          41

<210> SEQ ID NO 28
<211> LENGTH: 39
<212> TYPE: DNA
<213> ORGANISM: Artificial Sequence
<220> FEATURE:
<223> OTHER INFORMATION: Synthetic primer

<400> SEQUENCE: 28
```
atatatgcgg ccgcttgacg ggtattctga gcatcttac    39

<210> SEQ ID NO 29
<211> LENGTH: 38
<212> TYPE: DNA
<213> ORGANISM: Artificial Sequence
<220> FEATURE:
<223> OTHER INFORMATION: Synthetic primer

<400> SEQUENCE: 29
tatatactag tttgttttgt tgtttgtgt gatgaatt    38

<210> SEQ ID NO 30
<211> LENGTH: 33
<212> TYPE: DNA
<213> ORGANISM: Artificial Sequence
<220> FEATURE:
<223> OTHER INFORMATION: Synthetic primer

<400> SEQUENCE: 30
atatatgcgg ccgccctgct aaacacgccc tac    33

<210> SEQ ID NO 31
<211> LENGTH: 40
<212> TYPE: DNA
<213> ORGANISM: Artificial Sequence
<220> FEATURE:
<223> OTHER INFORMATION: Synthetic primer

<400> SEQUENCE: 31
atatatacta gttttgatt aaaattaaaa aactttttg    40

<210> SEQ ID NO 32
<211> LENGTH: 34
<212> TYPE: DNA
<213> ORGANISM: Artificial Sequence
<220> FEATURE:
<223> OTHER INFORMATION: Synthetic primer

<400> SEQUENCE: 32
atatatgcgg ccgctgaata cgtcctgtca attc    34

<210> SEQ ID NO 33
<211> LENGTH: 36
<212> TYPE: DNA
<213> ORGANISM: Artificial Sequence
<220> FEATURE:
<223> OTHER INFORMATION: Synthetic primer

<400> SEQUENCE: 33
atatatacta gttgaaattt gttgttttta gtaatc    36

<210> SEQ ID NO 34
<211> LENGTH: 35
<212> TYPE: DNA
<213> ORGANISM: Artificial Sequence
<220> FEATURE:
<223> OTHER INFORMATION: Synthetic primer

<400> SEQUENCE: 34
atatatgcgg ccgcatccga attcaatgta gcacc    35

<210> SEQ ID NO 35
<211> LENGTH: 37
<212> TYPE: DNA

<210> SEQ ID NO 35
<211> LENGTH: 37
<212> TYPE: DNA
<213> ORGANISM: Artificial Sequence
<220> FEATURE:
<223> OTHER INFORMATION: Synthetic primer

<400> SEQUENCE: 35
atatatacta gtgttttgtt gtggttattg gtagtac                              37

<210> SEQ ID NO 36
<211> LENGTH: 47
<212> TYPE: DNA
<213> ORGANISM: Artificial Sequence
<220> FEATURE:
<223> OTHER INFORMATION: Synthetic primer

<400> SEQUENCE: 36
agctagctag cggccgcgat ggaagatgca acttgcaaat gtagtcc                   47

<210> SEQ ID NO 37
<211> LENGTH: 47
<212> TYPE: DNA
<213> ORGANISM: Artificial Sequence
<220> FEATURE:
<223> OTHER INFORMATION: Synthetic primer

<400> SEQUENCE: 37
agctagctac tagtgttatt tttcttcttt gttctgtggg ttaaagg                   47

<210> SEQ ID NO 38
<211> LENGTH: 42
<212> TYPE: DNA
<213> ORGANISM: Artificial Sequence
<220> FEATURE:
<223> OTHER INFORMATION: Synthetic primer

<400> SEQUENCE: 38
agctagctag cggccgcgtt gaatgttagc gtcaacaaca ag                        42

<210> SEQ ID NO 39
<211> LENGTH: 47
<212> TYPE: DNA
<213> ORGANISM: Artificial Sequence
<220> FEATURE:
<223> OTHER INFORMATION: Synthetic primer

<400> SEQUENCE: 39
agctagctac tagtttgttt gtttatgtgt gtttattcga aactaag                   47

<210> SEQ ID NO 40
<211> LENGTH: 42
<212> TYPE: DNA
<213> ORGANISM: Artificial Sequence
<220> FEATURE:
<223> OTHER INFORMATION: Synthetic primer

<400> SEQUENCE: 40
agctagctag cggccgcgtt gaatgttagc gtcaacaaca ag                        42

<210> SEQ ID NO 41
<211> LENGTH: 37
<212> TYPE: DNA
<213> ORGANISM: Artificial Sequence
<220> FEATURE:
<223> OTHER INFORMATION: Synthetic primer

<400> SEQUENCE: 41
tatatactag tttgattgat ttgactgtgt tattttg                              37

<210> SEQ ID NO 42
<211> LENGTH: 1052
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (13)..(1011)

<400> SEQUENCE: 42

```
acagaattca ca atg gct act ttg aaa gat caa ttg att caa aat ttg ttg       51
              Met Ala Thr Leu Lys Asp Gln Leu Ile Gln Asn Leu Leu
                1               5                  10 aaa gaa gaa cat gtt cca caa aat aaa att act att gtt ggt gtt ggt         99
Lys Glu Glu His Val Pro Gln Asn Lys Ile Thr Ile Val Gly Val Gly
 15                  20                  25 gct gtt ggt atg gct tgt gct att tct att ttg atg aaa gat ttg gct       147
Ala Val Gly Met Ala Cys Ala Ile Ser Ile Leu Met Lys Asp Leu Ala
 30                  35                  40                  45 gat gaa gtt gct ttg gtt gat gtt atg gaa gat aaa ttg aaa ggt gaa       195
Asp Glu Val Ala Leu Val Asp Val Met Glu Asp Lys Leu Lys Gly Glu
                 50                  55                  60 atg atg gat ttg caa cat ggt tct ttg ttt ttg aga act cca aaa att       243
Met Met Asp Leu Gln His Gly Ser Leu Phe Leu Arg Thr Pro Lys Ile
             65                  70                  75 gtt tct ggt aaa gat tat aat gtt act gct aat tct aga ttg gtt att       291
Val Ser Gly Lys Asp Tyr Asn Val Thr Ala Asn Ser Arg Leu Val Ile
         80                  85                  90 att act gct ggt gct aga caa caa gaa ggt gaa tct aga ttg aat ttg       339
Ile Thr Ala Gly Ala Arg Gln Gln Glu Gly Glu Ser Arg Leu Asn Leu
     95                 100                 105 gtt caa aga aat gtt aat att ttt aaa ttt att att cca aat att gtt       387
Val Gln Arg Asn Val Asn Ile Phe Lys Phe Ile Ile Pro Asn Ile Val
110                 115                 120                 125 aaa tat tct cca aat tgt aaa ttg ttg gtt gtt tct aat cca gtt gat       435
Lys Tyr Ser Pro Asn Cys Lys Leu Leu Val Val Ser Asn Pro Val Asp
                130                 135                 140 att ttg act tat gtt gct tgg aaa att tct ggt ttt cca aaa aat aga       483
Ile Leu Thr Tyr Val Ala Trp Lys Ile Ser Gly Phe Pro Lys Asn Arg
            145                 150                 155 gtt att ggt tct ggt tgt aat ttg gat tct gct aga ttt aga tat ttg       531
Val Ile Gly Ser Gly Cys Asn Leu Asp Ser Ala Arg Phe Arg Tyr Leu
        160                 165                 170 atg ggt gaa aga ttg ggt gtt cat cca ttg tct tgt cat ggt tgg att       579
Met Gly Glu Arg Leu Gly Val His Pro Leu Ser Cys His Gly Trp Ile
    175                 180                 185 ttg ggt gaa cat ggt gat tct tct gtt cca gtt tgg tct ggt gtt aat       627
Leu Gly Glu His Gly Asp Ser Ser Val Pro Val Trp Ser Gly Val Asn
190                 195                 200                 205 gtt gct ggt gtt tct ttg aaa aat ttg cat cca gaa ttg ggt act gat       675
Val Ala Gly Val Ser Leu Lys Asn Leu His Pro Glu Leu Gly Thr Asp
                210                 215                 220 gct gat aaa gaa caa tgg aaa gct gtt cat aaa caa gtt gtt gat tct       723
Ala Asp Lys Glu Gln Trp Lys Ala Val His Lys Gln Val Val Asp Ser
            225                 230                 235 gct tat gaa gtt att aaa ttg aaa ggt tat act tct tgg gct att ggt       771
Ala Tyr Glu Val Ile Lys Leu Lys Gly Tyr Thr Ser Trp Ala Ile Gly
        240                 245                 250 ttg tct gtt gct gat ttg gct gaa tct att atg aaa aat ttg aga aga       819
Leu Ser Val Ala Asp Leu Ala Glu Ser Ile Met Lys Asn Leu Arg Arg
```

```
Leu Ser Val Ala Asp Leu Ala Glu Ser Ile Met Lys Asn Leu Arg Arg
    255                 260                 265 gtt cat cca att tct act atg att aaa ggt ttg tat ggt att aaa gaa      867
Val His Pro Ile Ser Thr Met Ile Lys Gly Leu Tyr Gly Ile Lys Glu
270                 275                 280                 285 gat gtt ttt ttg tct gtt cca tgt att ttg ggt caa aat ggt att tct      915
Asp Val Phe Leu Ser Val Pro Cys Ile Leu Gly Gln Asn Gly Ile Ser
                290                 295                 300 gat gtt gtt aaa gtt act ttg act cat gaa gaa gaa gct tgt ttg aaa      963
Asp Val Val Lys Val Thr Leu Thr His Glu Glu Glu Ala Cys Leu Lys
            305                 310                 315 aaa tct gct gat act ttg tgg ggt att caa aaa gaa ttg caa ttt taa     1011
Lys Ser Ala Asp Thr Leu Trp Gly Ile Gln Lys Glu Leu Gln Phe
        320                 325                 330 taactcgagc ttggttgaac acgttgccaa ggcttaagtg a                       1052

<210> SEQ ID NO 43
<211> LENGTH: 332
<212> TYPE: PRT
<213> ORGANISM: Artificial Sequence
<220> FEATURE:
<223> OTHER INFORMATION: Synthetic Construct

<400> SEQUENCE: 43

Met Ala Thr Leu Lys Asp Gln Leu Ile Gln Asn Leu Leu Lys Glu Glu
1               5                   10                  15

His Val Pro Gln Asn Lys Ile Thr Ile Val Gly Val Gly Ala Val Gly
                20                  25                  30

Met Ala Cys Ala Ile Ser Ile Leu Met Lys Asp Leu Ala Asp Glu Val
            35                  40                  45

Ala Leu Val Asp Val Met Glu Asp Lys Leu Lys Gly Glu Met Met Asp
        50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Arg Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
210                 215                 220

Glu Gln Trp Lys Ala Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255
```

```
Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
            275                 280                 285

Leu Ser Val Pro Cys Ile Leu Gly Gln Asn Gly Ile Ser Asp Val Val
        290                 295                 300

Lys Val Thr Leu Thr His Glu Glu Glu Ala Cys Leu Lys Lys Ser Ala
305                 310                 315                 320

Asp Thr Leu Trp Gly Ile Gln Lys Glu Leu Gln Phe
                325                 330

<210> SEQ ID NO 44
<211> LENGTH: 31
<212> TYPE: DNA
<213> ORGANISM: Artificial Sequence
<220> FEATURE:
<223> OTHER INFORMATION: Synthetic primer

<400> SEQUENCE: 44
atatatggat ccgcgtttat ttacctatct c                              31

<210> SEQ ID NO 45
<211> LENGTH: 31
<212> TYPE: DNA
<213> ORGANISM: Artificial Sequence
<220> FEATURE:
<223> OTHER INFORMATION: Synthetic primer

<400> SEQUENCE: 45
atatatgaat tctttgattg atttgactgt g                              31

<210> SEQ ID NO 46
<211> LENGTH: 34
<212> TYPE: DNA
<213> ORGANISM: Artificial Sequence
<220> FEATURE:
<223> OTHER INFORMATION: Synthetic primer

<400> SEQUENCE: 46
atatatctcg aggccagcta acttcttggt cgac                           34

<210> SEQ ID NO 47
<211> LENGTH: 31
<212> TYPE: DNA
<213> ORGANISM: Artificial Sequence
<220> FEATURE:
<223> OTHER INFORMATION: Synthetic primer

<400> SEQUENCE: 47
atatatgaat tctttgattg atttgactgt g                              31
```